US010086103B2

(12) United States Patent
Nakamoto et al.

(10) Patent No.: US 10,086,103 B2
(45) Date of Patent: Oct. 2, 2018

(54) CLOTHING TREATMENT APPARATUS

(71) Applicants:AQUA CO., LTD, Tokyo (JP);
QINGDAO HAIER WASHING MACHINE CO., LTD., Qingdao, Shandong (CN)

(72) Inventors: Shigeharu Nakamoto, Tokyo (JP); Hazime Suzuki, Tokyo (JP); Takayuki Nagai, Tokyo (JP); Tomohiro Yamauchi, Tokyo (JP); Osamu Tanikoshi, Tokyo (JP); Katsuji Onishi, Tokyo (JP)

(73) Assignee: Aqua Co., Ltd., Tokyo (JP)

( * ) Notice: Subject to any disclaimer, the term of this patent is extended or adjusted under 35 U.S.C. 154(b) by 0 days.

(21) Appl. No.: 15/573,384

(22) PCT Filed: May 13, 2016

(86) PCT No.: PCT/CN2016/082111
§ 371 (c)(1),
(2) Date: Nov. 10, 2017

(87) PCT Pub. No.: WO2016/180372
PCT Pub. Date: Nov. 17, 2016

(65) Prior Publication Data
US 2018/0093005 A1 Apr. 5, 2018

(30) Foreign Application Priority Data
May 13, 2015 (JP) .................................. 2015-098504

(51) Int. Cl.
*A61L 9/04* (2006.01)
*A61L 9/12* (2006.01)
*A61L 2/20* (2006.01)

(52) U.S. Cl.
CPC ................. *A61L 9/046* (2013.01); *A61L 2/20* (2013.01); *A61L 9/122* (2013.01); *A61L 2209/111* (2013.01); *A61L 2209/212* (2013.01)

(58) Field of Classification Search
None
See application file for complete search history.

(56) References Cited

U.S. PATENT DOCUMENTS 5,713,137 A * 2/1998 Fujita ...................... D06F 58/14
34/106
8,367,010 B2 2/2013 Chen et al.
(Continued)

FOREIGN PATENT DOCUMENTS

| CN | 2380593 | 5/2000 |
|---|---|---|
| CN | 201618175 | 11/2010 |

(Continued)

OTHER PUBLICATIONS

International Application No. PCT/CN2016/082111, International Search Report, dated Aug. 15, 2016.

*Primary Examiner* — Kishor Mayekar
(74) *Attorney, Agent, or Firm* — Greenberg Traurig, LLP

(57) ABSTRACT

A clothes deodorizing apparatus includes: a bag body for accommodating clothes; an ozone supply apparatus to supply air with the ozone into the bag body; a throwing inlet arranged on the bag body and opened and closed through a zipper; and a locking detection unit configured to detect that the throwing inlet is locked by the zipper. The locking detection unit includes: a detection lock connected with a slider of the zipper; and a lock detection part arranged on the ozone supply apparatus and configured to detect a lock inserting concave part that accepts the detection lock and the detection lock. The detection lock does not reach the lock inserting concave part in a state that the zipper is completely (Continued)

opened, and reaches the lock inserting concave part in a state that the zipper is completely closed.

4 Claims, 23 Drawing Sheets

(56) References Cited

U.S. PATENT DOCUMENTS

2002/0154011 A1* 10/2002 Pasin ...................... D06F 73/02
                                                                   340/540
2011/0194981 A1    8/2011  Chen et al.

FOREIGN PATENT DOCUMENTS

| CN | 102776771   | 11/2012 |
|----|-------------|---------|
| JP | 09262141    | 10/1997 |
| KR | 20120118288 | 10/2012 |

* cited by examiner

CLOTHING TREATMENT APPARATUS

The present application is a national phase application under 35 U.S.C. § 371 of International Patent Application PCT/CN2016/082111, filed on May 13, 2016, which claims priority to Japanese Patent Application No. 2015-098504, filed on May 13, 2015, the entire disclosures of which applications are hereby incorporated herein by reference.

TECHNICAL FIELD

The present disclosure relates to a clothes treating apparatus for implementing treatment, such as deodorization, on clothes.

BACKGROUND

In the past, a clothes refreshing apparatus is known. The clothes refreshing apparatus includes a storage bank capable of taking in clothes hung on a hanging rod. The high-temperature and high-humidity air circulates in the storage bank to absorb the smell of the clothes and is introduced to an ozone deodorizer, thereby deodorizing the clothes (with reference to a patent document 1).

Since the clothes refreshing apparatus includes the storage bank, the body of the apparatus often has a large size. Therefore, it is considered to develop a clothes treating apparatus, has a bag body for accommodating clothes and an ozone supply apparatus for supplying ozone-containing air into the bag body and is capable of implementing treatment, such as deodorization, on clothes accommodated in the bag body through ozone, in a manner of easy installation at home without a large installation space.

The clothes treating apparatus can adopt such a structure that a throwing inlet for clothes is arranged on the bag body and the throwing inlet is opened and closed by a zipper.

DOCUMENT ON PRIOR ART

Patent Document

Patent Document 1: Japanese Publication No. 04-327900

SUMMARY

Problems to be Solved

After the clothes are accommodated in the bag body, a user closes the zipper to lock a throwing inlet and then an ozone supply apparatus starts to operate. However, it can be contemplated that the user may sometimes mistakenly forget to close the zipper before the ozone supply apparatus starts to operate. In this case, such a hidden danger exists that ozone-containing air may leak from the throwing inlet and the clothes cannot be fully deodorized.

The present disclosure is directed to a technical solution completed in view of the problem. An object of the present disclosure is to provide a clothes treating apparatus capable of preventing operation in a state where the throwing inlet of a bag body is not locked by a zipper.

Solution for the Problems

In an primary implementation of the present disclosure, a clothes treating apparatus includes: a bag body configured to accommodate clothes; an ozone supply apparatus configured to supply ozone-containing air into the bag body; a throwing inlet arranged on the bag body and opened and closed through a zipper; and a locking detection unit configured to detect that the throwing inlet is locked by the zipper.

Through the above structure, the locking detection unit can detect that the throwing inlet of the bag body is locked by the zipper.

In the clothes treating apparatus in the present embodiment, the locking detection unit includes: a detected body connected with a slider of the zipper; an accepting part arranged on the ozone supply apparatus and configured to accept the detected body; and a detection part arranged on the ozone supply apparatus and configured to detect the detected body accepted by the accepting part. The detected body does not reach the accepting part in a state where the zipper is opened, and reaches the accepting part in a state where the zipper is closed.

Through the above structure, the locking detection unit capable of detecting the locking of the throwing inlet on an ozone supply apparatus side separated from the bag body can be realized.

When the above structure is adopted, then the detection part can adopt a structure including a relay rod and a detection switch; the relay rod is pressed and moved by the detected body in a state where the detected body is accepted by the accepting part; the detection switch is pressed by the relay rod through movement of the relay rod.

When the above structure is adopted, the direct contact between the detection switch and the user through the accepting part can be avoided, and the damage to the detection switch due to static electricity and the like can be avoided.

In the clothes treating apparatus in the present embodiment, the zipper is arranged on the throwing inlet in such a manner that the throwing inlet is locked when the slider of the zipper is pulled downwards and the throwing inlet is opened when the slider is pulled upwards.

Through the above structure, in a locking state of the throwing inlet, the self weight of the slider acts in the locking direction. Therefore, a hidden danger that a closed part of the zipper is opened due to the self weight of the slider does not exist, and the ozone-containing air can hardly leak from the closed part.

In the clothes treating apparatus in the present embodiment, the ozone supply apparatus includes: an exhaust port configured to exhaust the ozone-containing air supplied into the bag body; an ozone generator; a blowing fan configured to deliver air to the ozone generator; a vent pipe configured to guide the ozone-containing air generated by the ozone generator to the exhaust port; and a control part configured to control the ozone generator and the blowing fan. In this case, the control part enables the ozone generator and the blowing fan to operate based on locking of the throwing inlet detected by the locking detection unit.

Through the above structure, since the ozone generator and the blowing fan are not in operation when the detection part does not detect that the throwing inlet is locked by the zipper, operation in a state where the throwing inlet is not locked can be avoided.

Technical Effects

Through the present disclosure, a clothes treating apparatus capable of preventing operation in a state where the throwing inlet is not locked by the zipper can be provided.

Effects and significance of the present disclosure can be further clarified with the embodiments described below. However, the following embodiments are merely examples in the implementation of the present disclosure, and the content of the embodiments are not intended to limit the present disclosure.

DETAILED DESCRIPTION

A clothes deodorizing apparatus in an embodiment of a clothes treating apparatus of the present disclosure is described below with reference to drawings.

Figure 1:
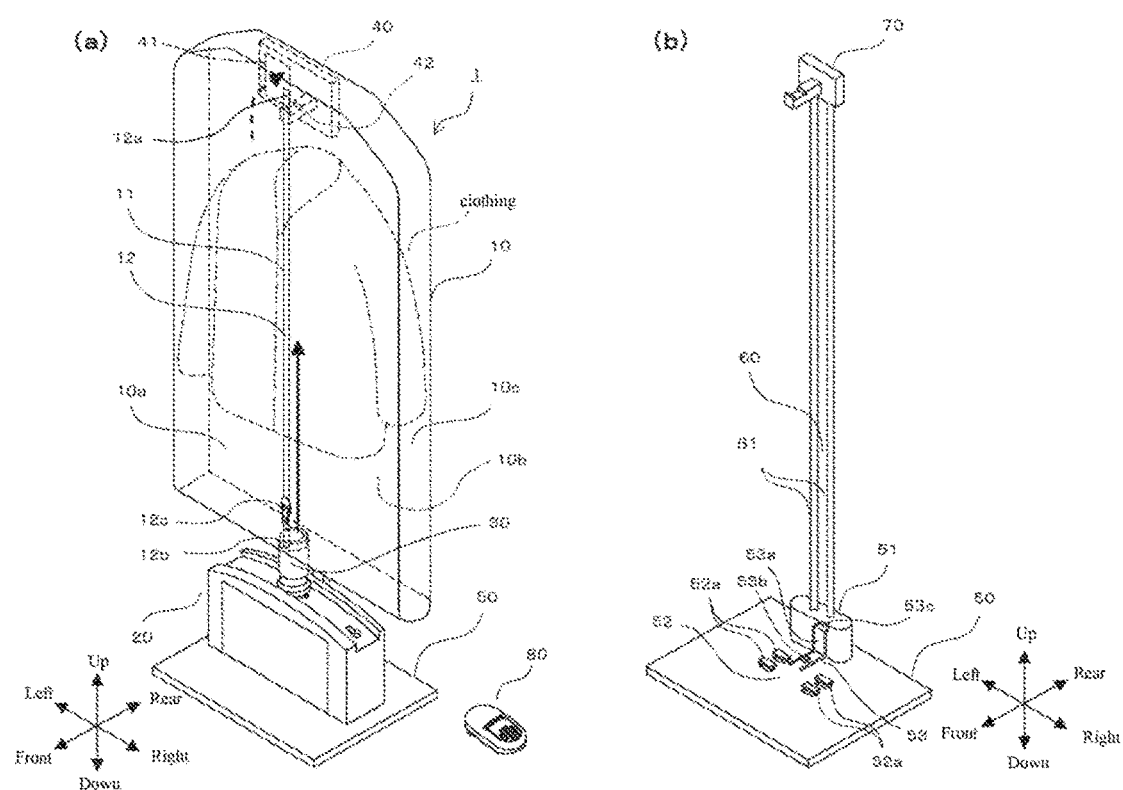
FIG. 1 is a structural diagram illustrating a clothes deodorizing apparatus of the embodiments.

FIG. 1 is a structural diagram illustrating a clothes deodorizing apparatus 1. FIG. 1(a) is a three-dimensional view of the clothes deodorizing apparatus 1. FIG. 1(b) is a three-dimensional view of a base 50, a column 60 and a bag body holding part 70 that form the clothes deodorizing apparatus 1.

Referring to FIG. 1, the clothes deodorizing apparatus 1 includes: a bag body 10, an ozone supply apparatus 20, an induction pipe 30, an exhaust and clothes rack holding unit 40, a base 50, a supporting column 60, a bag body holding part 70 and a fragrance supply unit 80.

The bag body 10 accommodates various clothes such as western-style clothes, coats. The bag body 10 is formed in a manner of overlapping a plurality of fabrics without air permeability so that tightness is adequate. The bag body 10 has an approximately lengthwise rectangular shape with its front and rear side flat, and is made of a front fabric 10a forming a front surface, a rear fabric 10b forming a rear surface and side fabrics 10c forming an upper, a lower, a left and a right side surfaces.

An up-down size of the bag body 10 is set to be capable of accommodating long clothes, e.g., long shirts, long coats. In addition, a front-rear size of the bag body 10 is set to be capable of accommodating one piece of clothes. It should be noted that the up-down size of the bag body 10 can also be set to be incapable of accommodating long clothes, and the front-rear size can also be set to be capable of accommodating about two or three pieces of clothes arranged in front and behind.

On the front surface of the bag body 10 and Approximately in the center of the front surface of the bag body 10 in the left-right direction, a gap that forms a throwing inlet for the clothes is formed from an upper end to a lower end. A zipper 12 is installed at the throwing inlet 11. A start part 12a and an ending part 12b of the zipper 12 in the case of locking are respectively located on the upper end and the lower end of the bag body 10. A slider 12c of the zipper 12 moves between the start part 12a and the end part 12b. When the slider 12c is pulled downwards from the start part 12a, the zipper 12 is closed so that the throwing inlet 11 is locked; and when the slider 12c is pulled upwards from the end part 12b, the zipper 12 is opened so that the throwing inlet 11 is opened. In this way, since a pull-down direction of the slider 12c is set as a locking direction of the throwing inlet 11, in a locking state of the throwing inlet 11, self weight of the slider 12c acts in the locking direction. Therefore, in comparison with the case where a pull-up direction of the slider 12c forms the locking direction of the throwing inlet 11, a hidden danger that the end part 12b, i.e., a closed part of the zipper 12, is opened due to the self weight of the slider 12c does not exist.

The ozone supply apparatus 20 performs deodorization operation for deodorizing the clothes and fragrance increasing operation for increasing fragrance on the clothes. During the deodorization operation, the ozone supply apparatus 20 performs an action of enabling exhausted air to contain ozone to supply ozone-containing air to the bag body 10. In addition, during the fragrance increasing operation, the ozone supply apparatus 20 performs an action of enabling the exhausted air not to contain the ozone to supply air without ozone to the bag body 10.

The induction pipe 30 is connected with the bag body 10 and the ozone supply apparatus 20 to guide the air exhausted from the ozone supply apparatus 20 into the bag body 10. During the deodorization operation, the ozone-containing air passes through the induction pipe 30; and during the fragrance increasing operation, the air without ozone passes through the induction pipe 30.

An exhaust and clothes rack holding unit 40 is arranged on an upper part of a rear surface of the bag body 10. The exhaust and clothes rack holding unit 40 integrally forms, using resin material, an exhaust part 41 having an ozone removing function and a clothes rack holding part 42 for holding a clothes rack for clothes to hang clothes. The ozone-containing air beneficial to clothes deodorization is exhausted from the bag body 10 through the exhaust part 41. When the air passes through the exhaust part 41, the ozone included in the air is removed.

The base 50 is a flat plate with a specified shape, such as a quadrangle. The ozone supply apparatus 20 is carried on the base 50. A supporting part 51 for supporting the supporting column 60 is formed at a rear of the base 50. Moreover, a first fixing part 52 and a second fixing part 53 for fixing the ozone supply apparatus 20 in a manner of enabling the front surface of the ozone supply apparatus 20 to face a direction of the front surface of the base 50 are formed on the base 50. The first fixing part 52 is composed of a plurality of hooked claw parts 52a. The second fixing part 53 includes: a L-shaped elastic rod 53a with one end supported by the base 50, a bulge 53b formed slightly back in relative to one end of the elastic rod 53a, and a pressing part 53c formed on the other end part of the elastic rod 53a. When the pressing part 53c is pressed downwards, the elastic rod 53a generates elastic deformation and the bulge 53b draw back into the lower part.

The supporting column 60 is composed of two rods 61. A lower end of the supporting column 60 is installed on the supporting part 51, and is erect in relative to the base 50. The supporting column 60 may be not composed of two rods 61, but composed of one or more than three rods. In addition, a telescopic mechanism capable of adjusting the height of the supporting column 60 can also be arranged on the supporting column 60.

A bag body holding part 70 is installed at an upper end of the supporting column 60. The bag body holding part 70 hangs and holds the bag body 10 in such a manner that the bag body 10 cannot move in any direction of front and rear, up and down and left and right.

The fragrance supply unit 80 is used when fragrance increasing operation is performed by the ozone supply apparatus 20. The fragrance supply unit 80 is detachably installed on the induction pipe 30, so that air supplied to the bag body 10 contains fragrant ingredients.

Next, structures of the bag body 10 and the induction pipe 30 and the exhaust and clothes rack holding unit 40 which are installed in the bag body 10 are described in detail.

Figure 2:
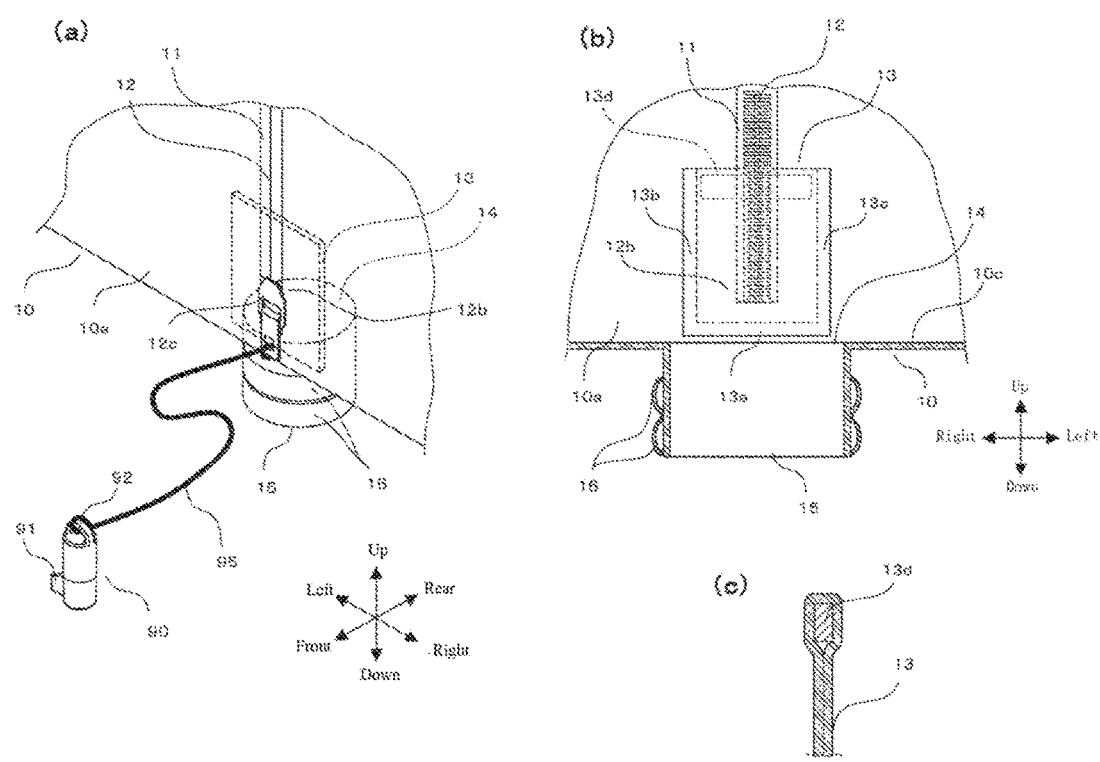
FIG. 2 is a diagram illustrating a lower central part of a bag body of the embodiments.
Figure 3:
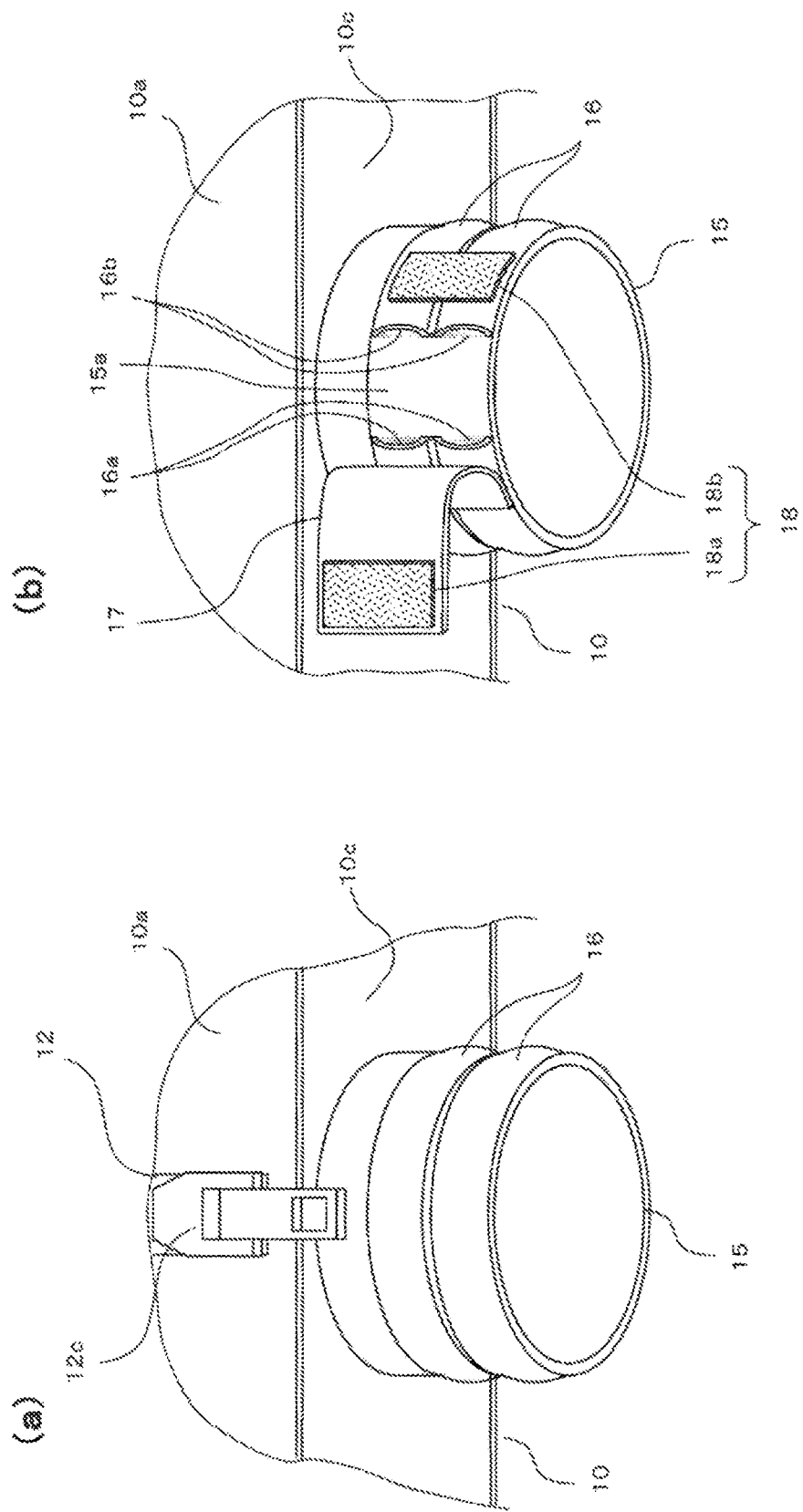
FIG. 3 is a diagram illustrating a lower central part of a bag body of the embodiments.

FIG. 2 and FIG. 3 are diagrams illustrating a lower central part of a bag body 10. FIG. 2(a) is a front three-dimensional view, and FIG. 2(b) is a rear section view. FIG. 3(a) is a three-dimensional view observed from a front lower part. FIG. 3(b) is a three-dimensional view observed from a rear lower part. FIG. 3(d) shows a side section of an upper part of an end hood 13.

At an inner surface of the front fabric 10a of the bag body 10, the end hood 13 is installed in a manner of covering the end part 12b of the zipper 12, i.e., the closed part, from an inner side of the bag body 10. The end hood 13 is a rectangle formed by fabrics without air permeability; a lower edge 13a, a right edge 13b and a left edge 13c are tightly fixed to the inner surface of the front fabric 10a through a fixing approach such as sewing, bonding.

When the zipper 12 is not adequately fully closed, the closed part of the zipper 12 can easily turn to a slightly open state. As mentioned above, a periphery of the closed part is covered by the end hood. During deodorization operation, the pressure in the bag body 10 is increased as the air is introduced into the bag body 10; then the end hood 13 is pushed to the front surface side of the bag body 10 and can easily be in tight contact with the inner surface of the front fabric 10a. Therefore, even if the closed part of the zipper 12 is slightly opened, the ozone-containing air can hardly leak through the closed part.

It should be noted that at an upper end part of the end hood 13, filling material 13d made of polyurethane rubber and the like is accommodated in the end hood 13 in such a manner that its thickness increases. Thus, the zipper 12 can be prevented from being engaged to the upper end part of the end hood 13 when the zipper 12 is closed.

To detect the locking of the throwing inlet 11 through the zipper 12, a detection lock 90 is connected with the slider 12c, and more specifically with a puller of the slider 12c, through a connecting rope 95. The detection lock 90 has a cylindrical shape. A protruding part 91 is formed at a lower end of a circumferential surface of the detection lock 90, and a hanging ring 92 for fixing the connecting rope 95 is formed at an upper end. The detection lock 90 is equivalent to the detected body of the present disclosure. One end part of the connecting rope 95 is connected with the handle of the slider 12c, and the other end is connected with the hanging ring 92. The connecting rope 95 may be a rope with a predetermined length, and for example, is realized by a silk ribbon, a chain, a metal wire and the like.

An air inlet 14 is formed in the central part of a lower surface of the bag body 10 and a cylindrical part 15 droops from the inlet 14. The cylindrical part 15 encircles a top end of the induction pipe 30 inserted into the inlet 14. The top end of the induction pipe 30 is fixed to the cylindrical part 15.

On an outer circumferential surface of the cylindrical part 15, belt penetrating parts 16, which are approximately circular, are arranged in a vertical parallel mode along a circumferential direction. Both ends of each belt penetrating part 16 are opened at a rear surface 15a of the cylindrical part 15 at the rear surface side forming the bag body 10. Each belt penetrating part 16 is used for the following bundle belt to penetrate through.

On an outer circumferential surface of the cylindrical part 15, to shield a rear surface 15a, a belt-shaped shielding part 17 is also arranged. One end of the shielding part 17 is installed near an open end 16a at one side of upper and lower belt penetrating parts 16. A surface having one side of a hook & loop 18, such as a hook surface 18a, is formed on the other end of the shielding part 17; and a surface having the other side of the hook & loop 18, such as a loop surface 18b, is formed near an open end 16b at the other side of upper and lower belt penetrating parts 16.

Figure 4:
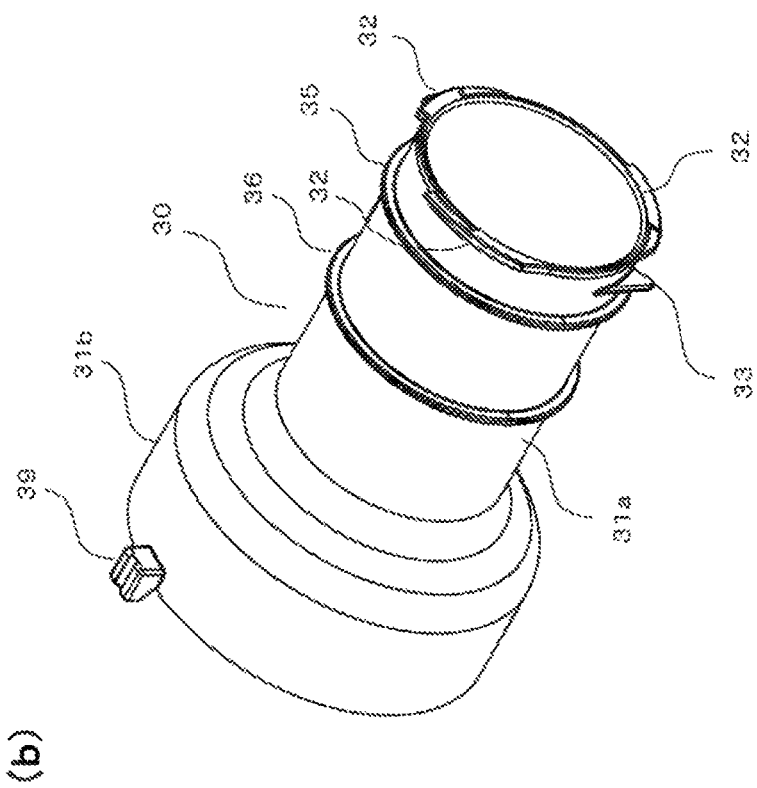
FIG. 4 is a structural diagram illustrating an induction pipe of the embodiments.
Figure 4:
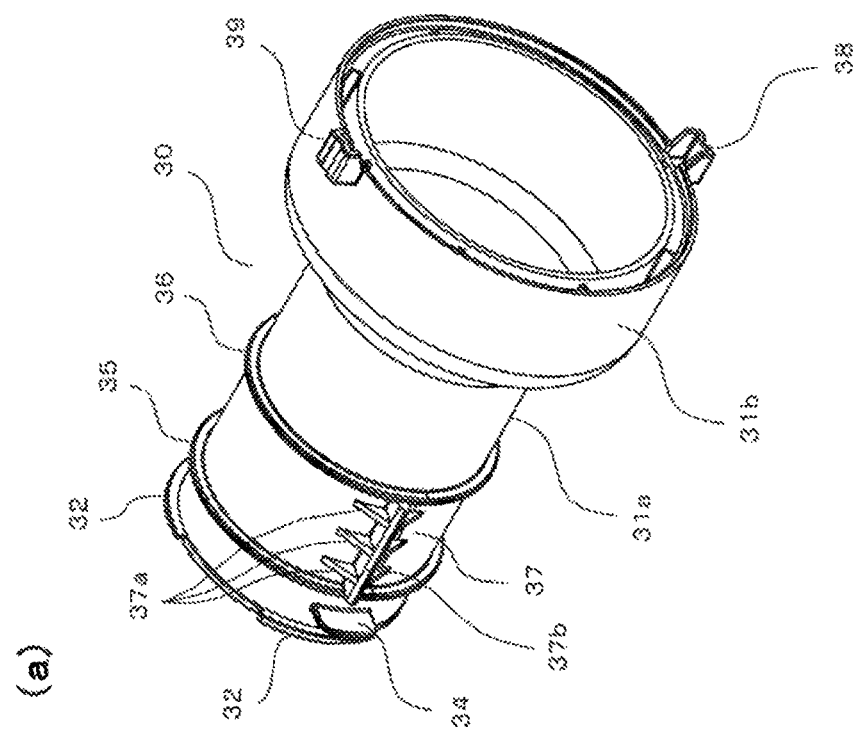

FIG. 4 is a structural diagram illustrating an induction pipe 30. FIG. 4(a) is a three-dimensional view observed from a lower side. FIG. 4(b) is a three-dimensional view observed from an upper side.

The induction pipe 30 includes a cylindrical main part 31a with a small outer diameter and a cylindrical connecting part 32b formed under the main part 31a and having a large outer diameter. A boundary part between the main part 31a and the connecting part 32b has a shape that outlines are gradually centralized together.

A plurality of clamping pieces 32 for fixing the fragrance supply unit 80 are formed at an upper end of the main part 31a. A front flange 33 and a rear flange 34 are formed in a position slightly lower than the clamping pieces 32 of the main part 31a and in positions that the induction pipe 30 faces a front side and a rear side of the bag body 10 in a state of being installed on the bag body 10. In a position slightly lower than the flange 33 and 34 of the main part 31a, annular upper flange 35 and lower flange 36 are formed at a specified interval along an up-down direction. A protruding strip 37 that vertically extends is formed between the upper flange 35 and the lower flange 36 and in a position of facing the rear of the bag body 10 in a state of installation on the bag body 10. The protruding strip 37 is formed in a shape approximate to a triangular prism through triangular ribs 37a vertically parallel and longitudinal ribs 37b for connecting the triangular ribs 37a.

A right claw part 38 and a left claw part 39 are respectively formed at a lower end of the connecting part 31b and in a position facing a right side of the bag body 10 and in a position facing a left side in a state of installation on the bag body 10.

Figure 5:
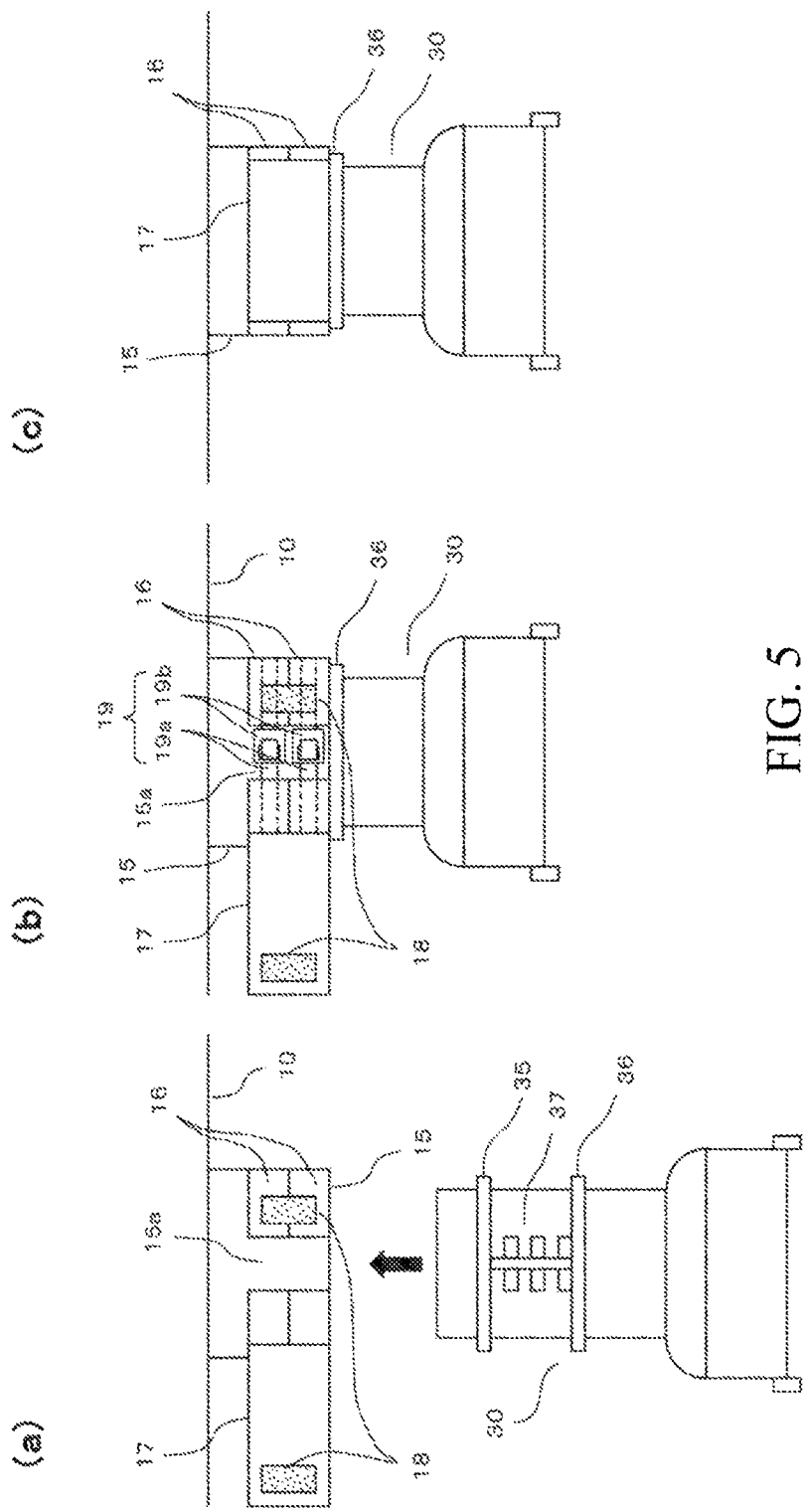
FIG. 5 is a schematic diagram illustrating a flow in which an induction pipe is installed on a bag body of the embodiments.

FIG. 5 is a schematic diagram illustrating a flow that an induction pipe 30 is installed on a bag body 10.

As shown in FIGS. 5(a) and (b), the induction pipe 30 is inserted into a position close to the lower flange 36 in the cylindrical part 15 in an orientation that the protruding strip 37 is located on the rear surface part 15a. As shown in FIG. 5(b), a bundling belt 19 is inserted into a belt penetrating 16, and the bundling belt 19 is wound on the cylindrical part 15. The bundling belt 19 is composed of a head 19a and a belt 19b. At a rear surface part 15a, the belt 19b penetrates through the head 19a, and the cylindrical part 15 is fastened to the inner side through the bundling belt 19. An excessive part of the belt 19b is cut off. Then, as shown in FIG. 5(c), the other end of the shielding part 17 is fixed to the belt penetrating 16 through a hook & loop 18. The head 19a is shielded by the shielding part 17. In this way, installation of the induction pipe 30 on the bag body 10 is completed.

Figure 6:
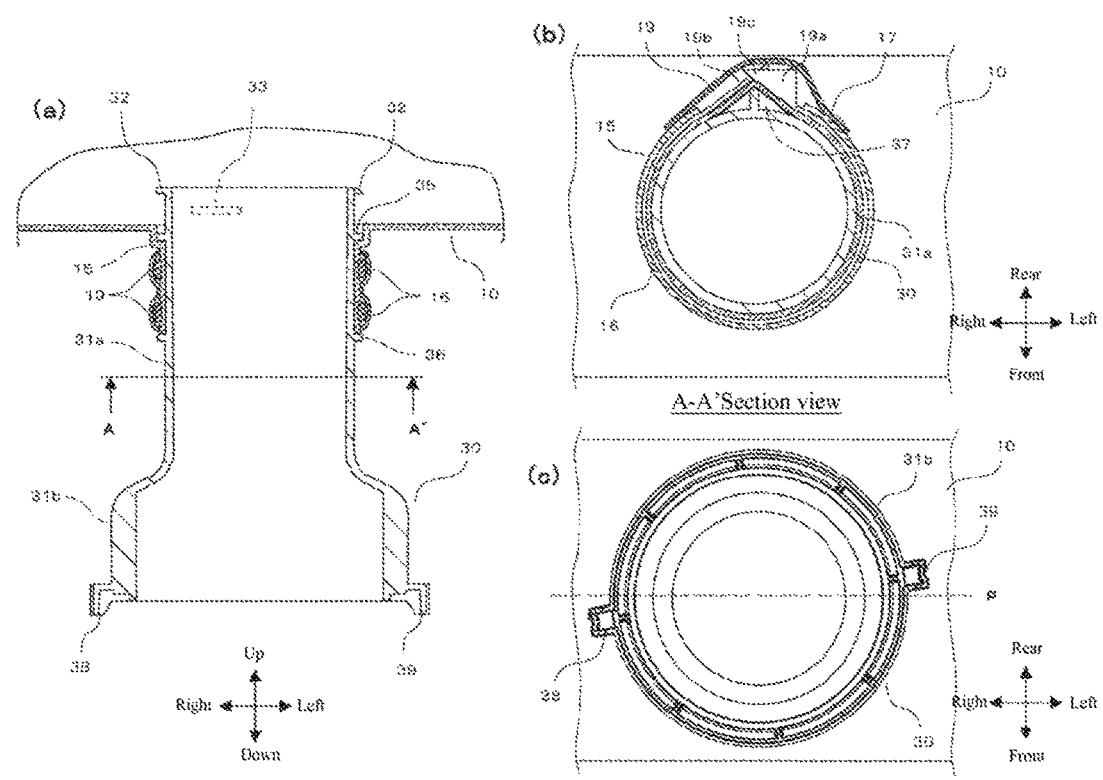
FIG. 6 is a diagram illustrating a lower central part of a bag body in a state of having an induction pipe installed of the embodiments.

FIG. 6 is a diagram illustrating a lower central part of a bag body 10 in a state of installing an induction pipe 30. FIG. 6(a) is a rear section view illustrating a lower central part of a bag body 10. FIG. 6(b) is an A-A' section view of FIG. 6(a). FIG. 6(c) is a diagram of a lower central part of a bag body 10 observed from a lower side.

As shown in FIG. 6(a), in a state that the induction pipe 30 is installed on the cylindrical part 15 of the bag body 10, the upper and the lower flanges 35 and 36 and the bundling belt 19 are clamped along the up-down direction, so that the induction pipe 30 is fixed to the cylindrical part 15 along the up-down direction. Namely, the induction pipe 30 passes through the lower flange part 36, and does not move upwards or enter the bag body 10; and passes through the upper flange 35, and does not move downwards or separate from the bag body 10. Moreover, as shown in FIG. 6(b), a combination part 19c of the head 19a and the belt 19b of the bundling belt 19 is clamped with the protruding strip 37 of the induction pipe 30 along the circumferential direction. Thus, the induction pipe 30 is fixed to the cylindrical part 15 along the circumferential direction. In this way, the induction pipe 30 is installed in a manner of not separating from the bag body 10 and also not rotating relative to the bag body 10. In addition, the right claw part 38 and the left claw part 39 of the induction pipe 30 present a predetermined position relationship relative to the bag body 10. Namely, as shown in FIG. 6(c), the right claw part 38 is in a position slightly forward than a center line P of the front-rear direction of the bag body 10, and the left claw part 39 is in a position slightly backward than the center line P of the front-rear direction of the bag body 10.

As shown in FIG. 6(a), the top part of the induction pipe 30 protrudes in a manner of being closer to the upper part than the lower surface of the bag body 10. The front flange 33 and the rear flange 34 are in positions slightly close to the upper part than the lower surface of the bag body 10.

Figure 7:
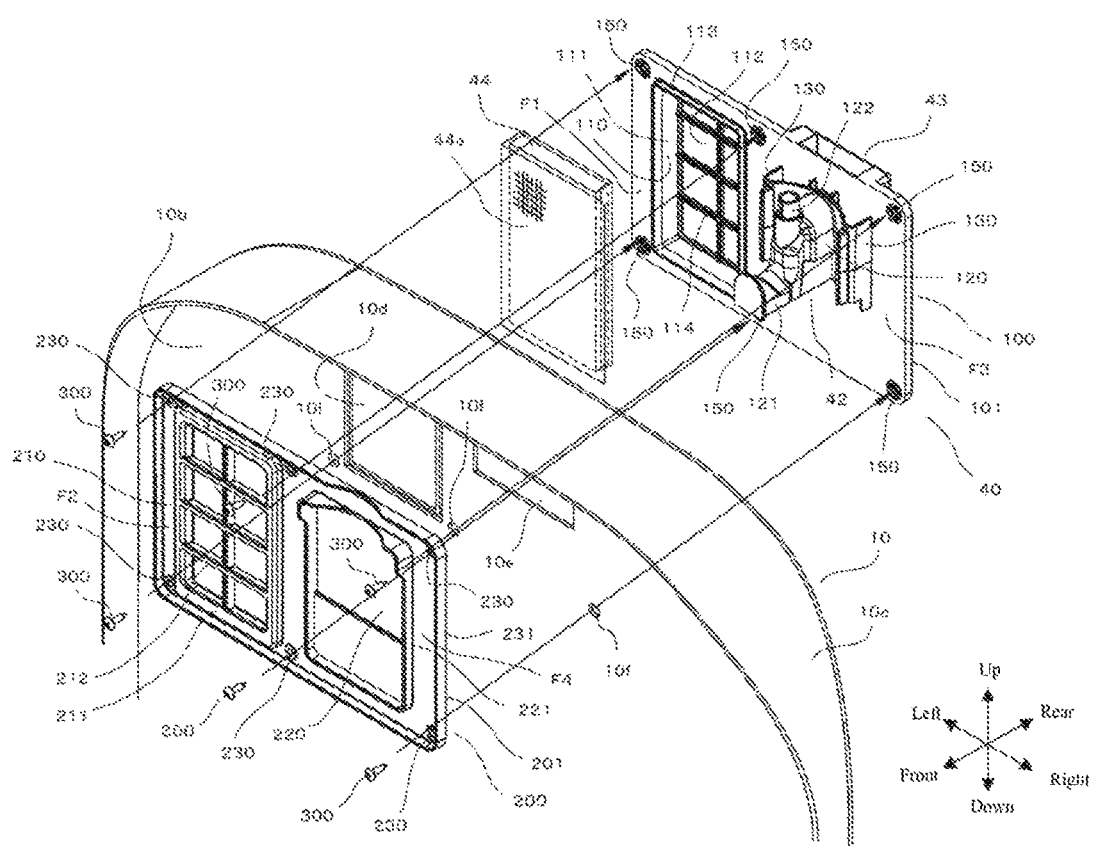
FIG. 7 is a structural diagram illustrating an exhaust and clothes rack holding unit of the embodiments.
Figure 8:
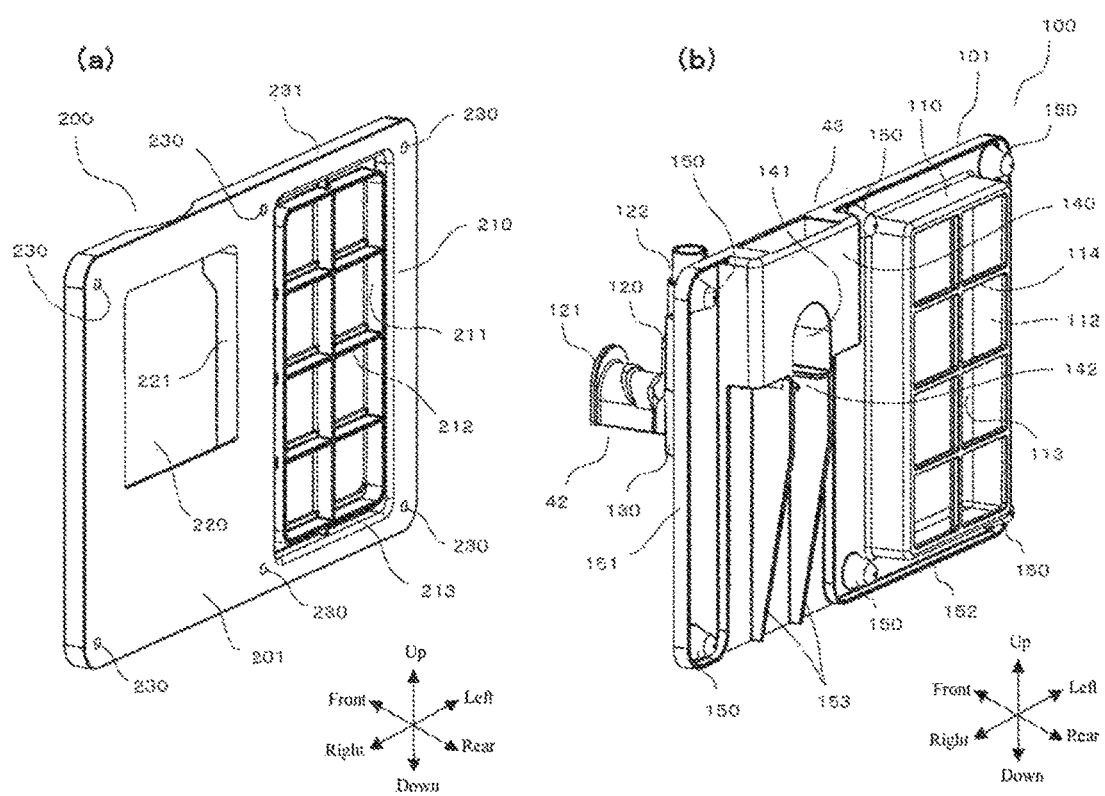
FIG. 8 is a structural diagram illustrating an exhaust and clothes rack holding unit of the embodiments.
Figure 9:
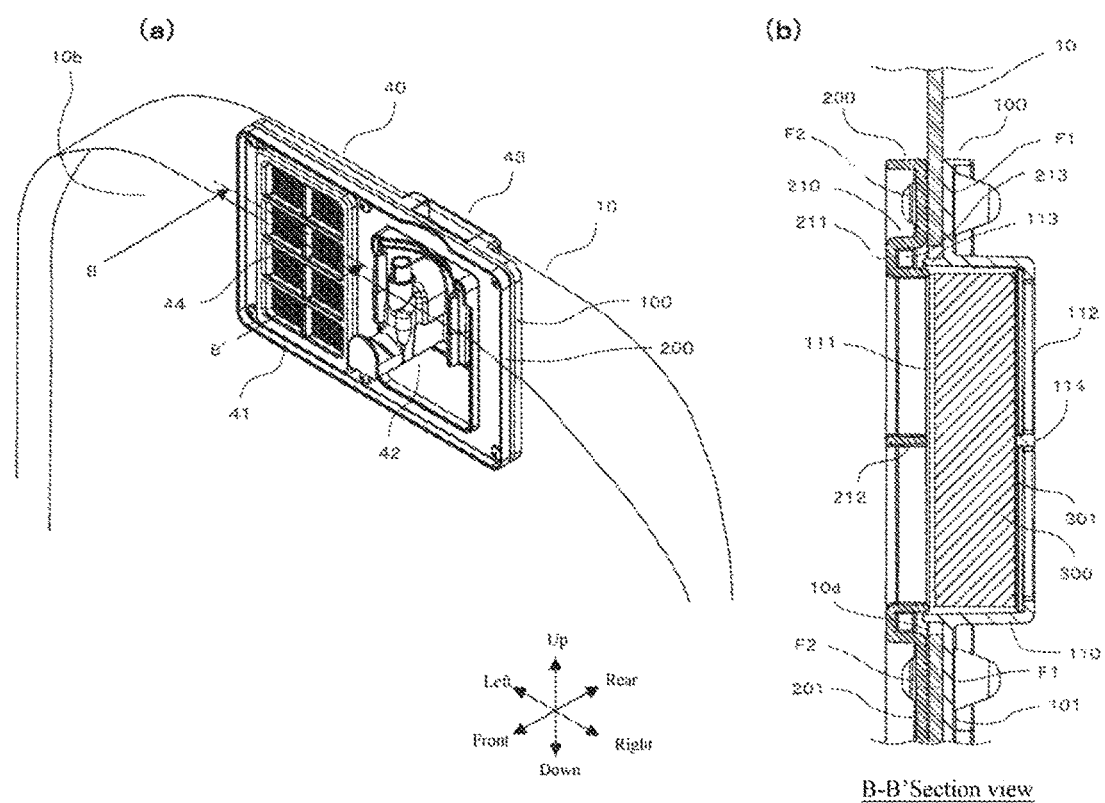
FIG. 9 is a structural diagram illustrating an exhaust and clothes rack holding unit of the embodiments.
Figure 10:
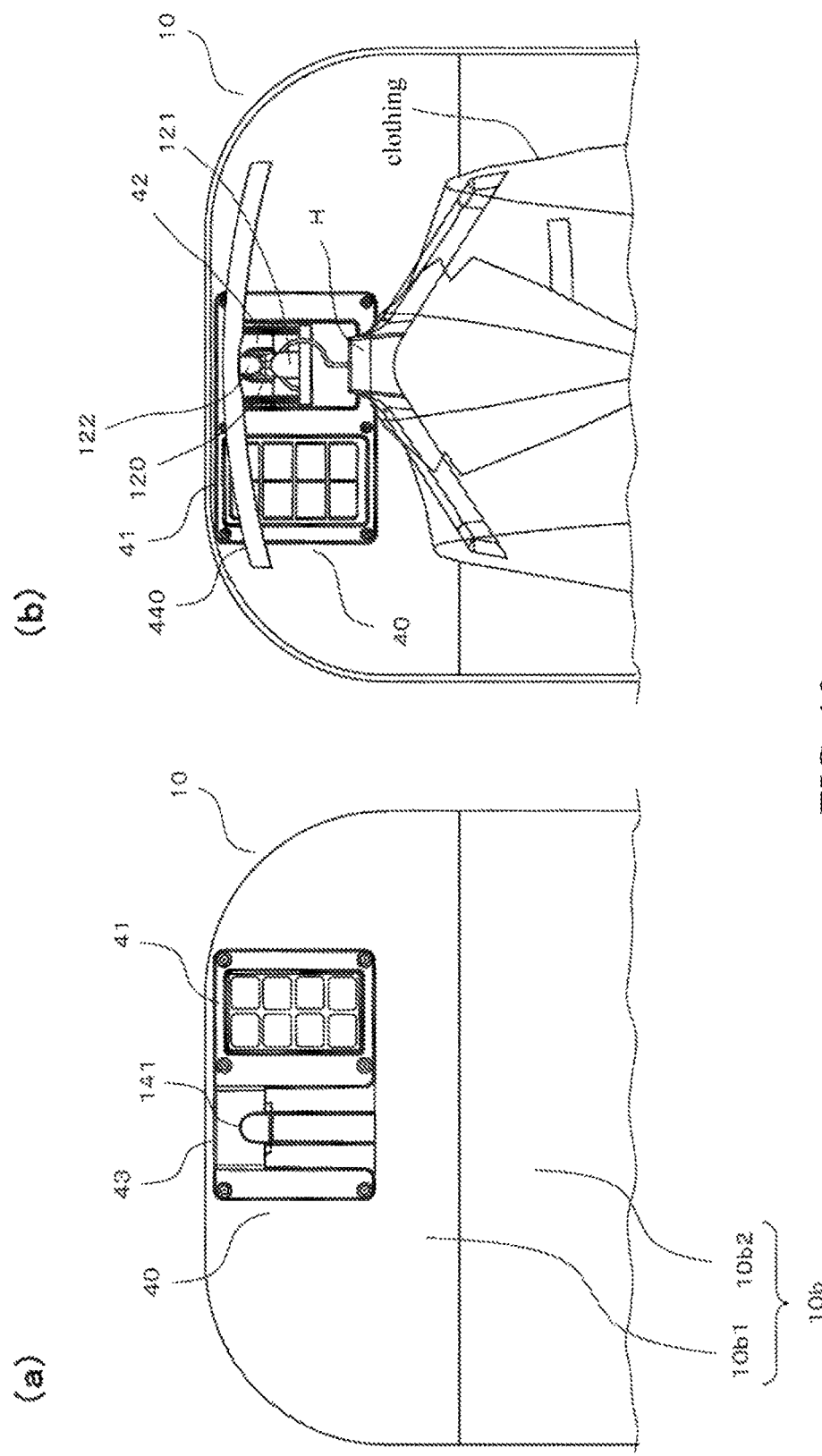
FIG. 10 is a structural diagram illustrating an exhaust and clothes rack holding unit of the embodiments.

FIGS. 7 to 10 are structural diagrams illustrating an exhaust and clothes rack holding unit 40. FIG. 7 is a three-dimensional diagram illustrating an exploded exhaust and clothes rack holding unit 40 before installed on a bag body 10. FIGS. 8(a) and (b) are respectively rear three-dimensional diagrams illustrating a front unit 200 and a rear unit 100 forming an exhaust and clothes rack holding unit 40. FIG. 9(a) is a three-dimensional diagram illustrating an exhaust and clothes rack holding unit 40 installed on a bag body 10. FIG. 9(b) is a B-B' section view of FIG. 9(a) of the exhaust part 41 along a horizontal direction. FIGS. 10(a) and (b) are respectively a rear view and a main view illustrating an upper part of a bag body 10. It should be noted that a front surface of the bag body 10 is not shown in FIGS. 7 and 10(b) for convenience, and the bag body 10 is drawn to be transparent in FIG. 9(a).

As for the exhaust and clothes rack holding unit 40, the exhaust part 41 is formed at its left half part, and the clothes rack holding part 42 is formed at its front side of a right half part. Moreover, an installation part 43 for installing the bag body holding part 70 is formed at a rear side of the right half part of the exhaust and clothes rack holding unit 40.

The exhaust and clothes rack holding unit 40 is formed by combining the rear unit 100 and the front unit 200. The rear unit 100 and the front unit 200 are made of a material (e.g., resin) which is harder than the material of the bag body 10. The rear unit 100 and the front unit 200 respective parts of an exhaust part 41, a clothes rack holding part 42 and an installation part 43 on lalongate rectangular rear plate 101 and front plate 201.

The exhaust part 41 includes an exhaust pipe 110 formed on the rear plate 101 and a pipe hood 210 formed on the front plate 201. An ozone removing filter 44 is installed in the exhaust part 41. The exhaust pipe 110 is formed in a manner of protruding backwards, and is rectangular. An opening is formed on the front surface of the exhaust pipe 110 as an inlet/outlet 111 of the ozone removing filter 44, and an opening is formed on the rear surface of the exhaust pipe 110 as an air outlet 112. The circumferential edge of the inlet/outlet 111 is enclosed by a guide frame 113 which protrudes forwards. A lattice 114 is formed at the air outlet 112. The pipe hood 210 is formed in a manner of protruding forwards slightly, and includes a rectangular outer frame 211 and a lattice 212 formed in the outer frame 211. The thickness of the outer frame 211 is greater than the thickness of the lattice 212, and a groove 213 is formed at an inner side of the outer frame 211.

The ozone removing filter 44 has a rectangular shape with flat front and rear surfaces. The ozone removing filter 44 can use, for example, an activated carbon/catalyst filter formed by transferring the activated carbon and the catalyst to a base material such as aluminum. The ozone removing filter 44 covers the periphery of the ozone removing filter 44 through a meshed hood 44a in a manner of not being touched by hands. It should be noted that the ozone removing filter 44 can also use other filters with an ozone removing effect, such as a photocatalyst ceramic filter.

The clothes rack holding part 42 includes a first holding part 120 extending from the front surface of the rear plate 101 to the front side and a second holding part 121 formed in front of the first holding part 120. A cylindrical inserting port 122 which protrudes upwards is formed in the first holding part 120. The second holding part 121 has an upward hook shape.

On the front surface of the rear plate 101, guide bodies 130 are formed on a left side and a right side of the clothes rack holding part 42. In addition, an opening 220 through which the clothes rack holding part 42 and the left and right guide bodies 130 penetrate are formed in the front plate 201. A frame body 221 is formed around the opening 220.

The installation part 43 includes a body 140 and an installation hole 141. The body 140 is formed in a square box shape, and protrudes backwards from the rear surface of the rear plate 101. The installation hole 141 is formed on the rear surface of the body 140, and extends to the inner of the clothes rack holding part 42 across the rear plate 101. A notch part 142 is formed on the lower surface of the installation hole 141 in a manner of facing the inner from an opening end of the installation hole 141.

Screw holes 230 through which screws 300 go are formed in the circumferential position of the front plate 201 and in positions of the upper and lower ends of the center of the left-right direction. Moreover, reinforcing ribs 231 which extend all over the entire circumference are formed at an outer circumferential edge of the front surface of the front plate 201.

Installation protrusions 150 for fixing the screws 300 are formed in the circumferential position of the rear plate 101 and in positions of the upper and lower ends of the center of the left-right direction. In addition, on the rear surface of the rear plate 101, a first reinforcing rib 151 which encircles the outer edge of the rear plate 101 from the right upper end of the body part 140 and connects the right lower end of the body 140 is formed at the right side of the installation part 43. A second rib 152 which encircles the outer edge of the rear plate 101 from the left upper end of the body 140 and connects the left lower end of the body part 140 is formed at the left side of the installation part 43. Moreover, two third reinforcing ribs 153 which extend from both sides of the installation hole 141 to the lower side are formed on the rear surface of the rear plate 101.

On the upper part of the rear surface of the bag body 10, a first opening 10d is formed in a position corresponding to the exhaust part 41, and second openings 10e are formed in positions corresponding to the clothes rack holding part 42 and the left and the right guide bodies 130. In addition, on the upper part of the rear surface of the bag body 10, insertion holes 10f are formed in positions corresponding to the screw holes 230 of the front plate 201 and the installation protrusions 150 of the rear plate 101.

When the exhaust and clothes rack holding unit 40 is assembled, the ozone removing filter 44 is accommodated in the exhaust pipe 110 of the rear unit 100 at first. Next, the guide frame 113 is inserted into the first opening 10d, and the left and the right guide bodies 130 are inserted into the second openings 10e. The rear unit 100 is installed on the upper part of the rear surface of the bag body 10 from the outer side of the bag body 10. Next, the front unit 200 is installed on the rear unit 100 from the inner side of the bag body 10. Then, the front unit 200 and the rear unit 100 combined by horizontally clamping the upper part of the rear surface of the bag body 10. In this way, as shown in FIG. 9(a), the exhaust and clothes rack holding unit 40 is installed on the upper part of the rear surface of the bag body 10 when being assembled.

Herein, when the rear unit 100 is installed on the rear surface of the bag body 10, the guide frame 113 and the guide bodies 130 are respectively inserted into the first opening 10d and the second openings 10e for guidance. Thus, the rear unit 100 can be easily installed on the bag body 10, and the assembly of the exhaust and clothes rack holding unit 40 becomes easy.

In addition, as shown in FIG. 9(b), on the exhaust part 41, the top of the guide frame 113 of the exhaust pipe 110 is embedded into the groove 213 of the outer frame of the pipe hood 210. Thus, since the sealing effect between the exhaust pipe 110 and the pipe hood 210 is enhanced, the ozone-containing air passing through the exhaust part 41 can hardly leak from the exhaust part 41.

Then, a flat part around the exhaust pipe 110 of the rear plate 101 functions as a rear flange F1 covering the circumference of the first opening 10d from the outer side, and a flat part around the pipe hood 210 of the front plate 201 functions as a front flange F2 covering the circumference of the first opening 10d from the inner side. As shown in FIG. 9(b), when the exhaust part 41 is installed on the first opening 10d, the first opening 10d is in a state that the circumference is sealed by the rear flange F1 and the front flange F2. Thus, the ozone-containing air in the bag body 10 can hardly leak through the first opening 10d.

Similarly, a flat part around the clothes rack holding part 42 of the rear plate 101 and the left and right guide bodies 130 functions as a rear flange F3 covering the circumference of the second openings 10e from the outer side, and a flat part around the opening 220 of the front plate 201 functions as a front flange F4 covering the circumference of the second opening 10e from the inner side. When the clothes rack holding part 42 is installed on the second openings 10e, the second openings 10e are in a state that the circumference is sealed by the rear flange F3 and the front flange F4. Thus, the ozone-containing air in the bag body 10 becomes can hardly leak through the second openings 10e.

In a state that an exhaust and clothes rack holding unit 40 is installed on an upper part of a rear surface of the bag body 10, as shown in FIG. 10(a), the installation hole 141 of the installation part 43 is in a center of the bag body 10 in horizontal direction. In addition, as shown in FIG. 10(b), the clothes rack holding part 42 is arranged in the bag body 10 and located in a central part of the bag body 10 in horizontal direction. A hook of the clothes rack H for clothes to hang the clothing is hooked on the second holding part 121 of the clothes rack holding part 42, and an upper mask 440 is installed at an inserting port 122 of the first holding part 120. The upper mask 440 is formed in a lalongate platy shape slightly bent into an arch. The upper surface of the bag body 10 is strengthened from an inner side through the upper mask 440.

The upper part 10b1 of the rear fabric 10b on the upper part of the rear surface forming the bag body 10 is harder than other parts 10b2 by making the thickness on the upper part become larger than that on other parts 10b2 of the rear fabric 10b or changing the material of the fabric of other parts 10b2. Thus, the exhaust and clothes rack holding unit 40 can be reliably held through the upper part of the rear surface of the bag body 10.

The structure of the bag body holding part 70 and the installation structure of the bag body 10 on the bag body holding part 70 are described in detail below.

Figure 11:
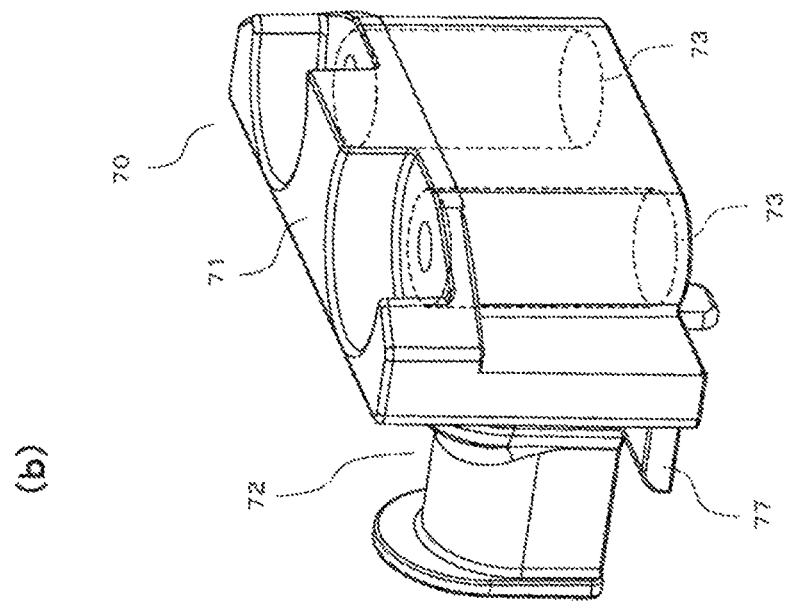
FIG. 11 is a structural diagram illustrating a bag body holding part of the embodiments.
Figure 11:
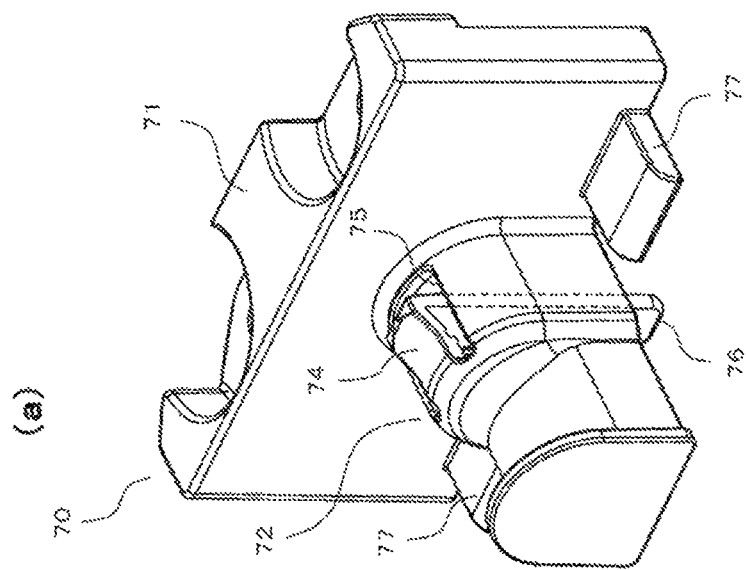
Figure 12:
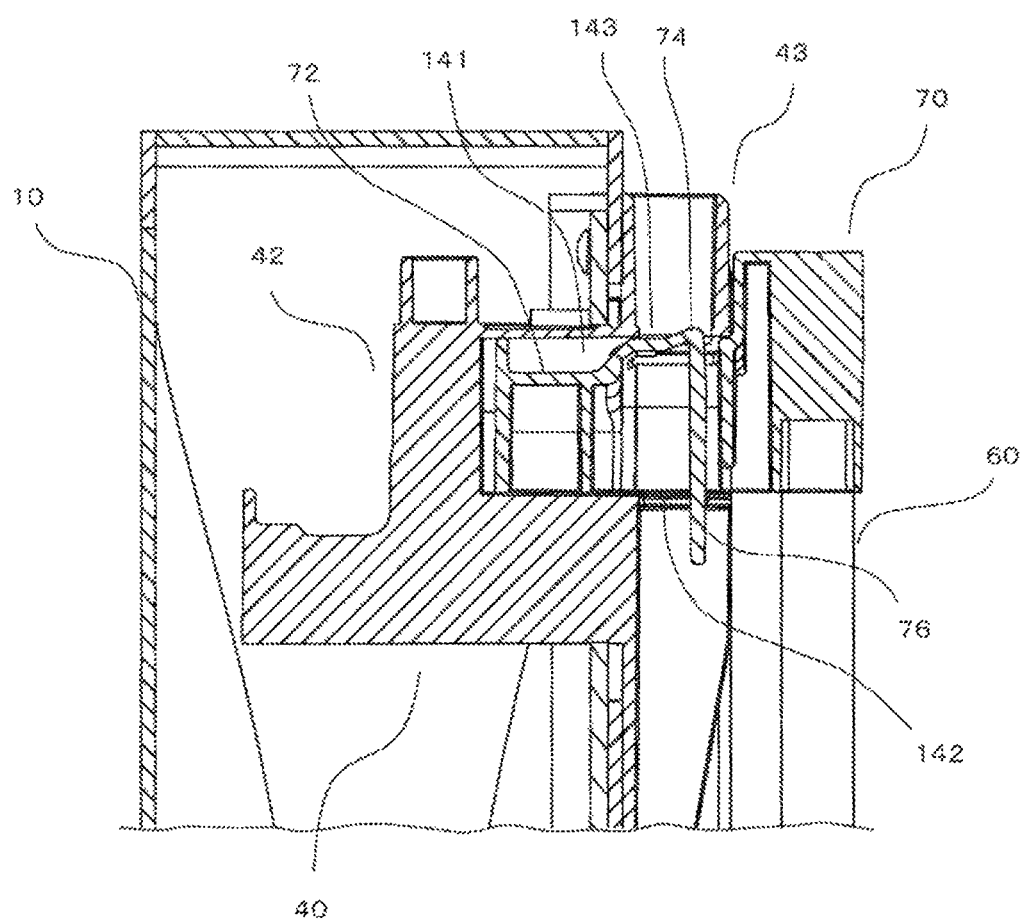
FIG. 12 is a longitudinal section view illustrating a main part in a state where the bag body is installed on a bag body holding part of the embodiments.

FIG. 11 is a structural diagram illustrating a bag body holding part 70. FIG. 11(a) is a front three-dimensional diagram, and FIG. 11(b) is a rear three-dimensional diagram. FIG. 12 is a longitudinal section view illustrating a main part in a state that the bag body 10 is installed on a bag body holding part 70.

The bag body holding part 70 includes a box-shaped body 71 and a holding part 72 which extends forwards from the body 71. Cylindrical insertion holes 73 are formed in left and right sides of the body 71. An upper end of a rod 61 is inserted into an insertion hole 73.

A clamping claw 74 is formed on an upper part of a root part of the holding part 72. An opening 75 is formed around the clamping claw 74. An inner part of the holding part 72 is made hollow, and an operation sheet 76 which droops from the clamping claw 74 protrudes to the lower part of the holding part 72 from the inner parts of the opening 75 and the holding part 72. When the operation sheet 76 is pulled to the lower side, the clamping claw 74 draws back into the lower side.

The top of the holding part 72 has an upward hook shape. When the bag body 10 is not installed on the bag body holding part 70, the clothes rack for clothes can be hooked to the top. At a lower end of the front surface of the body 71, supporting sheets 77 are formed on the left side and the right side of the holding part 72.

As shown in FIG. 12, under a condition that the bag body 10 is installed on the bag body holding part 70, the holding part 72 of the bag body holding part 70 is inserted into the installation hole 141 of the exhaust and clothes rack holding unit 40. During the insertion, the operation sheet 76 of the holding part 72 passes through the notch 142 of the installation hole 141. A clamping hole 143 is formed in the upper part of the inlet of the installation hole 141. When the holding part 72 is inserted into the end of the installation hole 141, the clamping claw 74 is clamped with the clamping hole 143. Thus, the holding part 72 is not separated from the installation hole 131. The bag body 10 is fixed in a manner of not moving vertically and horizontally and not moving forwards relative to the bag body holding part 70. In addition, the lower surface of the installation part 43, although not shown in FIG. 12, is supported by left and right supporting sheets 77. As shown in FIG. 1(*a*), in a state of being fixed to the bag body holding part 70, the front surface of the bag body 10 faces the front direction of the base 50.

The operation sheet 76 is pulled to the lower part so that the clamping claw 74 draws back and the bag body 10 moves forward, thereby removing the bag body 10 from the bag body holding part 70.

The detailed structure of the ozone supply apparatus 20 is described below.

Figure 13:
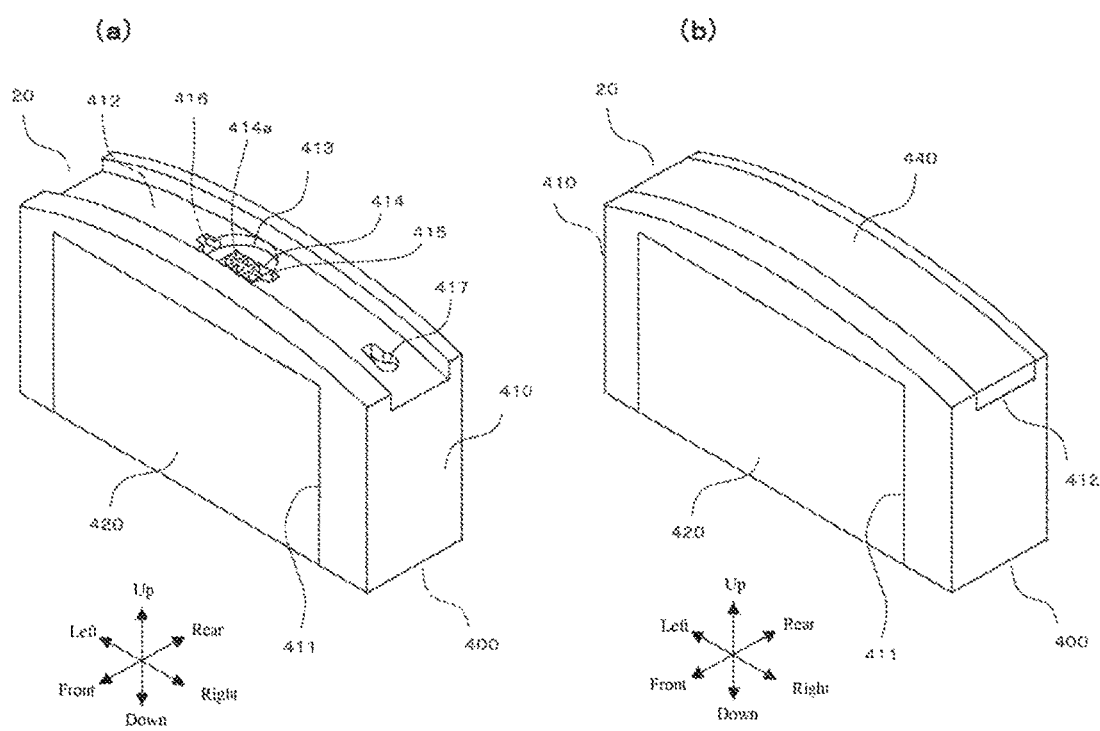
FIG. 13 is a structural diagram illustrating an ozone supply apparatus of the embodiments.
Figure 14:
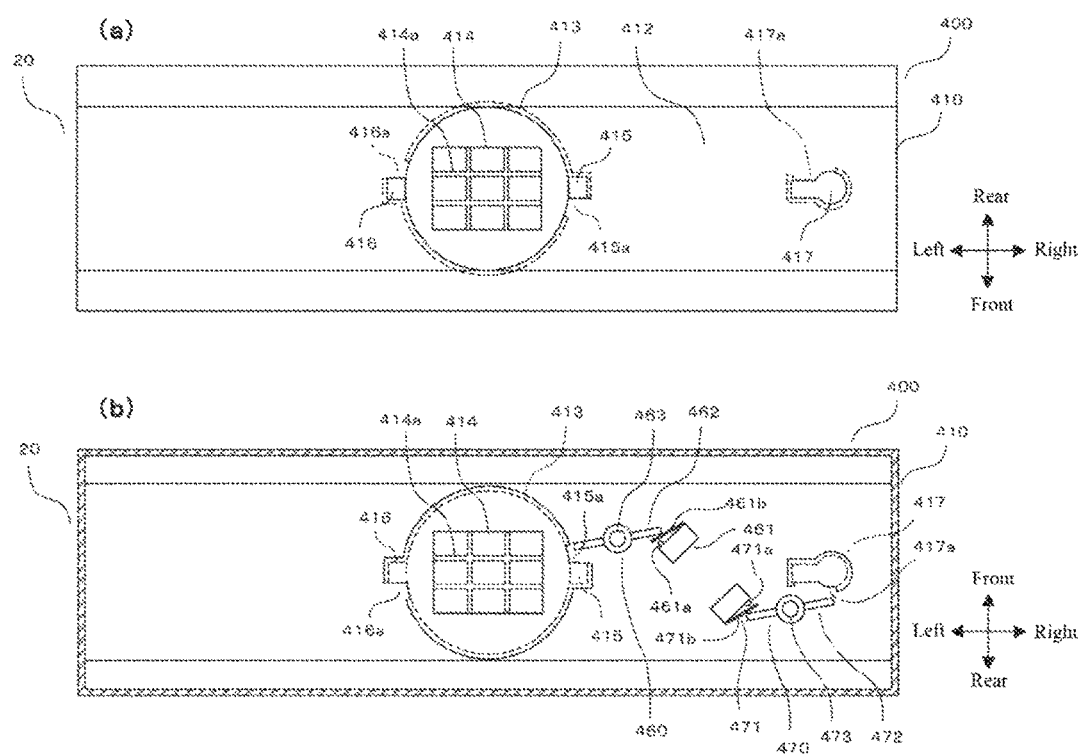
FIG. 14 is a structural diagram illustrating an ozone supply apparatus involved in embodiments.
Figure 15:
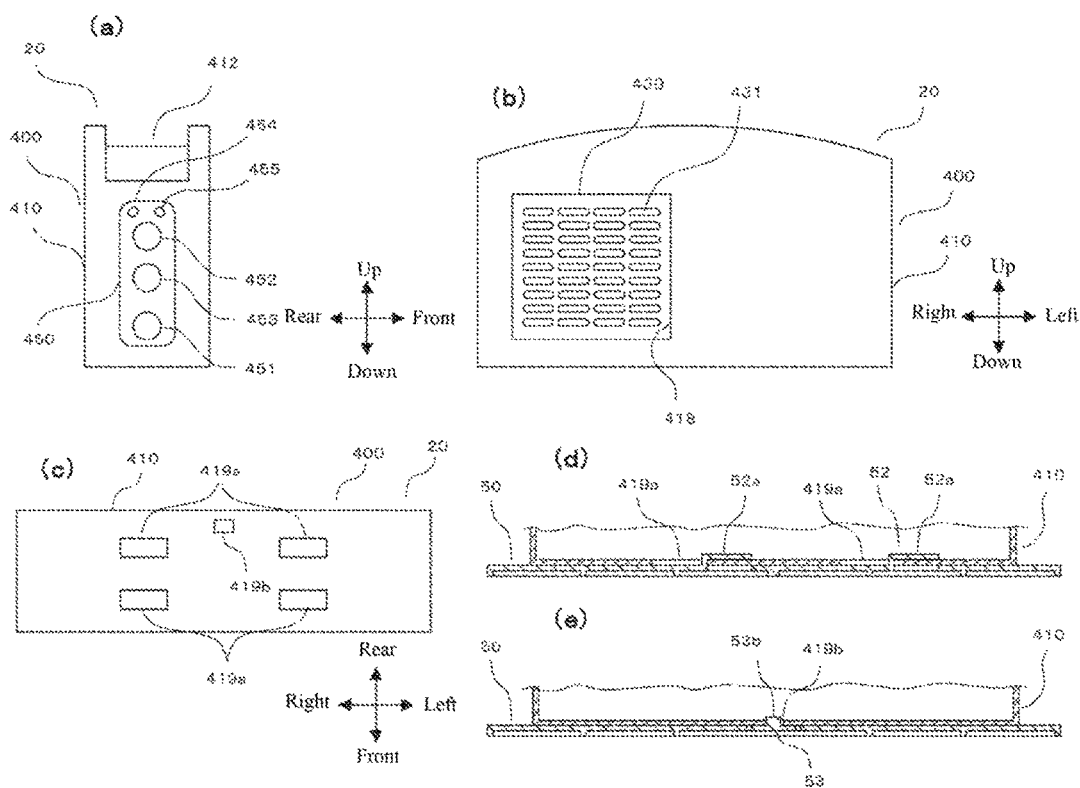
FIG. 15 is a structural diagram illustrating an ozone supply apparatus of embodiments.
Figure 16:
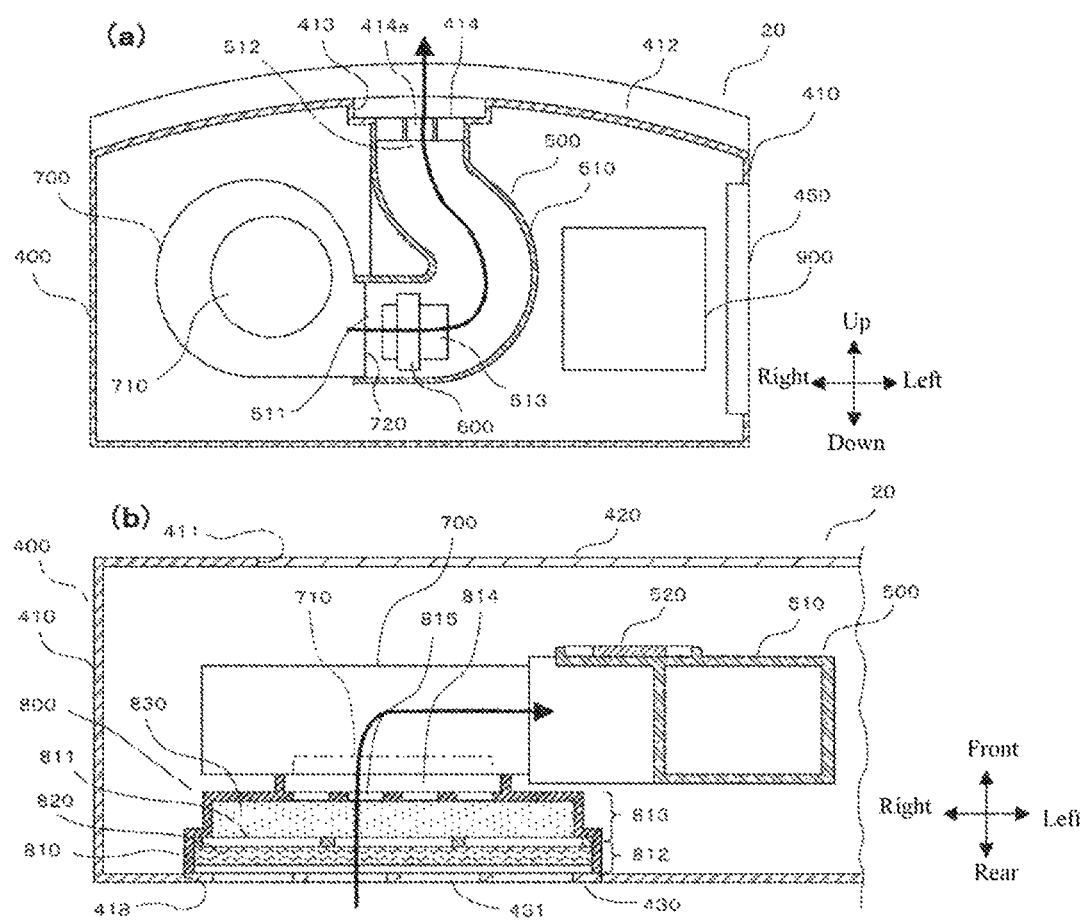
FIG. 16 is a structural diagram illustrating an ozone supply apparatus of the embodiments.

FIGS. 13 to 16 are structural diagrams illustrating an ozone supply apparatus 20. FIG. 13(*a*) is a three-dimensional diagram illustrating an ozone supply apparatus 20 in a state without installing an upper mask 440. FIG. 13(*b*) is a three-dimensional diagram illustrating an ozone supply apparatus 20 in a state with an upper mask 440. FIG. 14(*a*) is a top view illustrating an ozone supply apparatus 20. FIG. 14(*b*) is a transverse section view of an upper surface of a shell 400 of an ozone supply apparatus 20 observed from an inner side. FIGS. 15(*a*) to (*c*) are a left view, a rear view and a bottom view illustrating an ozone supply apparatus 20 respectively. FIGS. 15(*d*) and (*e*) are side section views illustrating a main part of an ozone supply apparatus 20 in a state of being fixed to the base 50. FIG. 16(*a*) is a longitudinal section view for observing an ozone supply apparatus 20 from a rear. FIG. 16(*b*) is a transverse section view for overlooking a main part of an ozone supply apparatus 20. It should be noted that a right inserting concave part 415, a left inserting concave part 416, a lock inserting concave 417, a pipe detection part 460 and a lock detection part 470 are not shown in FIG. 16(*a*).

The ozone supply apparatus 20 includes a shell 400, a vent pipe 500, an ozone generator 600, a blowing fan 700, an air suction unit 800 and a control unit 900.

The shell 400 includes: a shell body 410, a front mask 420, an air suction hood 430, an upper mask 440 and an operation part 450. As shown in FIG. 13(*a*), the shell body 410 has a lalongate rectangular shape with an upper surface gently bent. A front surface opening 411 is formed on a front surface of the shell body 410. The front surface opening 411 is detachably locked through the front mask 420.

On the upper surface of the shell body 410, a concave part 412 sunk into a shape identical with that of the upper mask 440 is formed. An inserting port 413 sunk into a circular shape is arranged in the center of the concave part 412. An exhaust port 414 with a latticed rectification rib 414*a* is formed in the inserting port part 413.

At the concave part 412, a right inserting concave part 415 and a left inserting concave part 416 with shapes corresponding to the right claw part 38 and the left claw part 39 of the induction pipe 30 are formed on the left side and the right side of the inserting port part 413. As shown in FIGS. 14(*a*) and (*b*), at a front side of the right inserting concave part 415, a right opening 415*a* is formed in such a manner that the right claw part 38 inserted into the right inserting concave part 415 only moves to a right direction by about an amount of one right claw part 38. Similarly, at a rear side of the left inserting concave part 416, a left opening 416*a* is formed in such a manner that the left claw part 39 inserted into the left inserting concave part 416 only moves to a right direction by about an amount of one left claw part 39.

At the concave part 412, the lock inserting concave part 417 with a shape corresponding to the detection lock 90 is formed at a right end. As shown in FIGS. 14(*a*) and (*b*), an opening 417*a* is formed in a side surface of the rear side of the lock inserting concave part 417. The lock inserting concave part 417 is equivalent to the accepting part of the present disclosure.

As shown in FIG. 13(*b*), when the clothes deodorizing apparatus 1 is not used, the upper mask 440 removed from the bag body 10 can be installed on the concave part 412. Thus, since a holding place of the upper mask 440 removed from the bag body 10 is ensured, the upper mask 440 can be prevented from being lost when it is not used. In addition, dust can be prevented from entering the shell 400 through the exhaust port 414 and the lock inserting concave part 417 when the clothes deodorizing apparatus is not used.

As shown in FIG. 14(*b*), the pipe detection part 460 and the lock detection part 470 are configured at an inner side of the upper surface of the shell body 410. The pipe detection part 460 includes a detection switch 461 and a relay rod 462. The detection switch 461 has a switch 461*a* and a rod 461*b* for pressing the switch 461*a*. The relay rod 462 is installed in a free rotation mode on a rotating shaft 463 formed at the inner side of the upper surface of the shell body 410. One end of the relay rod 462 is located near the right inserting concave part 415, and the other end is in contact with the detection switch 461. The lock detection part 470 includes a detection switch 471 and a relay rod 472. The detection switch 471 has a switch part 471*a* and a rod part 471*b* for pressing the switch part 471*a*. The relay rod 472 is installed in a free rotation mode on a rotating shaft 473 formed at the inner side of the upper surface of the shell body 410. One end of the relay rod 472 is located near the lock inserting concave part 417, and the other end is in contact with the detection switch 471. The lock detection part 470 is equivalent to the detection part of the present disclosure.

As shown in FIG. 15(*a*), the operation part 450 is arranged on a left side surface of the shell body 410. The operation part 450 includes a power button 451, a deodorization button 452 and a fragrance increasing button 453. The power button 451 is a button for switching on and switching off a power supply of the clothes deodorizing apparatus 1. The deodorization button 452 is a button for starting deodorization operation. The fragrance increasing button 453 is a button for starting fragrance increasing operation. In addition, the operation part 450 includes a first informing part 454 and a second informing part 455. The first informing part 454 is, for example, composed of a LED, which is illuminated to inform that the induction pipe 30 is not connected with the ozone supply apparatus 20. The second informing part 455 is, for example, composed of a LED, which is illuminated to inform that the throwing inlet 11 of the bag body 10 is not locked.

As shown in FIG. 15(b), an air suction port 418 is formed in a rear surface of the shell body 410. The air suction port 418 is detachably locked through the air suction hood 430. A plurality of air suction holes 431 are formed in the air suction hood 430.

As shown in FIG. 15(c), at a bottom surface of the shell body 410, a first installation hole 419a is formed in a position corresponding to each claw part 52a of the first fixing part 52 of the base 50. A second installation hole 419b is formed in a position corresponding to the bulge 53b of the second fixing part 53. After the pressing part 53c of the second fixing part 53 is pressed downwards to make the bulge 53b to draw back, when the claw part 52a loads the ozone supply apparatus 20 on the base 50 through the first installation hole 419a so as to transversely slide the ozone supply apparatus 20, as shown in FIG. 15(d), the claw part 52a is clamped with a bottom surface of the shell body 410. Then, when the pressing on the pressing part 53c stops, as shown in FIG. 15(e), the bulge 53b is embedded into the second installation hole 419b. Thus, the ozone supply apparatus 20 is fixed to the base 50 in a manner of not moving in directions of up and down, front and rear and left and right. Therefore, the ozone supply apparatus 20 can be prevented from falling due to a force applied to the ozone supply apparatus 20 when the bag body 10 is inflated because of the air supplied by the ozone supply apparatus 20.

A vent pipe 500, an ozone generator 600, a blowing fan 700, an air suction unit 800 and a control unit 900 are arranged in the shell 400.

As shown in FIGS. 16(a) and (b), the vent pipe 500 includes a pipe body 510 and a pipe cover 520. An induction port 511 of the pipe body 510 is connected with the exhaust port 720 of the blowing fan 700, and an eduction port 512 is connected with the exhaust port 414. The ozone generator 600 is arranged near the induction port 511 in the pipe body 510. The pipe body 510 has the following shape: the pipe body 510 extends upwards to the eduction port 512 after bending in a manner of extending from the induction port 511 to the left and beginning to go back to the right over the part where the ozone generator 600 is arranged. Namely, a part of a downstream side of the pipe body 510 forming the ozone generator 600 crawls in an S shape.

The ozone generator 600 is a discharge type ozone generator. Discharge such as corona discharge and silent discharge is generated between a pair of electrodes, and ozone is generated from the air between a pair of electrodes. At a front surface of the pipe body 510, an opening 513 is formed in a position corresponding to the ozone generator 600. The opening 513 is locked through the pipe cover 520. The front mask 420 and the pipe cover 520 may be removed, such that the electrodes are cleaned through the opening part 513 to maintain the ozone generator 600.

The blowing fan 700 is a centrifugal fan. A suction inlet 710 is arranged in a side surface, and an exhaust port 720 is arranged in a circumferential surface. The suction inlet 710 is opposite to the air suction port 418 on the rear surface of the shell 400. The blowing fan 700 obtains the air through the suction inlet 710, and delivers the obtained air to the ozone generator 600 in the vent pipe 500. The blowing fan 700 can also use other fans besides the centrifugal fan, such as an axial flow fan.

As shown in FIG. 16(b), an air suction unit 800 is arranged between the air suction port 418 of the shell 400 and the suction inlet 710 of the blowing fan 700. The air suction unit 800 includes an air suction pipe 810, a dust filter 820 and an ozone removing filter 830.

The air suction pipe 810 is divided into a first filter accommodating part 812 at a side of the air suction port 418 and a second filter accommodating part 813 at a side of the blowing fan 700 through a latticed dividing plate 811. A dust filter 820 is accommodated at the first filter accommodating part 812, and an ozone removing filter 830 is accommodated at the second filter accommodating part 813. The dust filter 820 removes dust included in the air obtained from the air suction port 418. The ozone removing filter 830 removes the ozone included in the air passing through the dust filter 820. The ozone removing filter 830, which is identical with the ozone removing filter 44 of the exhaust and clothes rack holding unit 40, can use an activated carbon/catalyst filter.

The air suction pipe 810 is provided with a connecting part 814 connected with the suction inlet 710 of the blowing fan 700. The connecting part 814 is connected with the second filter accommodating part 813 through a communication hole 815.

The control unit 900 includes a CPU, a memory to control the ozone generator 600 and the blowing fan 700. The control unit 900 is equivalent to the control part of the present disclosure.

Figure 17:
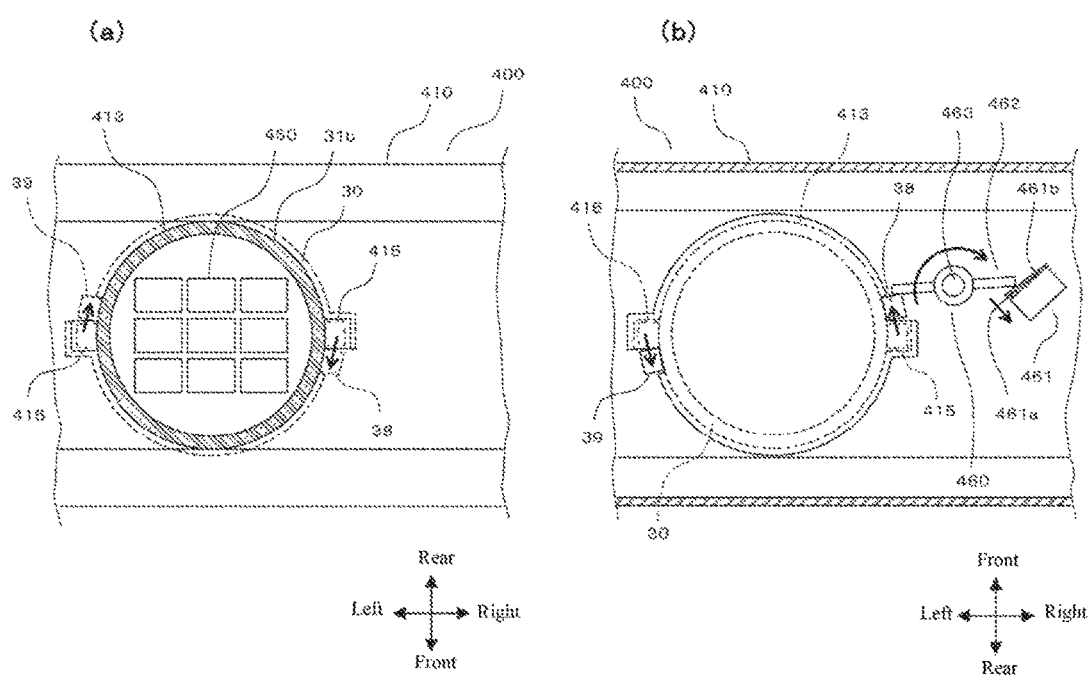
FIG. 17 is a diagram illustrating a connection of an induction pipe to an ozone supply apparatus and connection detection through a pipe detection part of the embodiments.

Next, with reference to FIG. 17, the connection of the induction pipe 30 to the ozone supply apparatus 20 and the connection detection through the pipe detection part 460 are described.

When the induction pipe 30 is connected with the ozone supply apparatus 20, as shown in FIG. 17(a), the connecting part 31b of the induction pipe 30 is inserted into the inserting port part 413 in a manner of respectively inserting the right claw part 38 and the left claw part 39 into the right inserting concave part 415 and the left inserting concave part 416. Then, when the induction pipe 30 rotates to the right in a top view, the right claw part 38 and the left claw part 39 respectively move to the inner side of the upper surface of the shell body 410 through the right opening part 415a and the left opening part 416a, and are clamped with the upper surface of the shell body 410. Thus, the induction pipe 30 does not fall to the upper part.

As described in FIG. 6(c), since the right claw part 38 is in a position slightly forward than a center line P of the front-rear direction of the bag body 10, and the left claw part 39 is in a position slightly backward than the center line P of the front-rear direction of the bag body 10, as shown in FIG. 1(a), the induction pipe 30 is connected with the ozone supply apparatus 20 in such a manner that the front surface of the bag body 10 faces the front direction of the ozone supply apparatus 20, i.e., the front direction of the base 50. In addition, as mentioned above, the exhaust and clothes rack holding unit 40 is fixed to the bag body holding art 70 in such a manner that the front surface of the bag body 10 faces the front direction of the base 50. Therefore, the bag body 10 is hung above the ozone supply apparatus 20 in such a state that the upper part and the lower part can hardly be distorted. Thus, the clothes can be well accommodated in the bag body 10, and the ozone-containing air can successfully circulate in the bag body 10.

In this way, the induction pipe 30 is connected with the ozone supply apparatus 20. As shown in FIG. 17(b), when the right claw part 38 moves to the inner of the upper surface of the shell body 410, one end of the relay rod 462 is pressed by the right claw part 38. The relay rod 462 rotates; a rod 461b is pressed by the other end of the relay rod 462; and a switch 461a is pressed by the pressed rod 461b. Thus, the detection switch 461 detects that the induction pipe 30 is installed on the inserting port 413.

It should be noted that when the induction pipe 30 is removed from the inserting port part 413, the rod part 461b rotates the relay rod 462 through its elasticity, and simultaneously returns to an initial position. Thus, the detection switch 461 detects that the induction pipe 30 is removed from the inserting port part 413.

Figure 18:
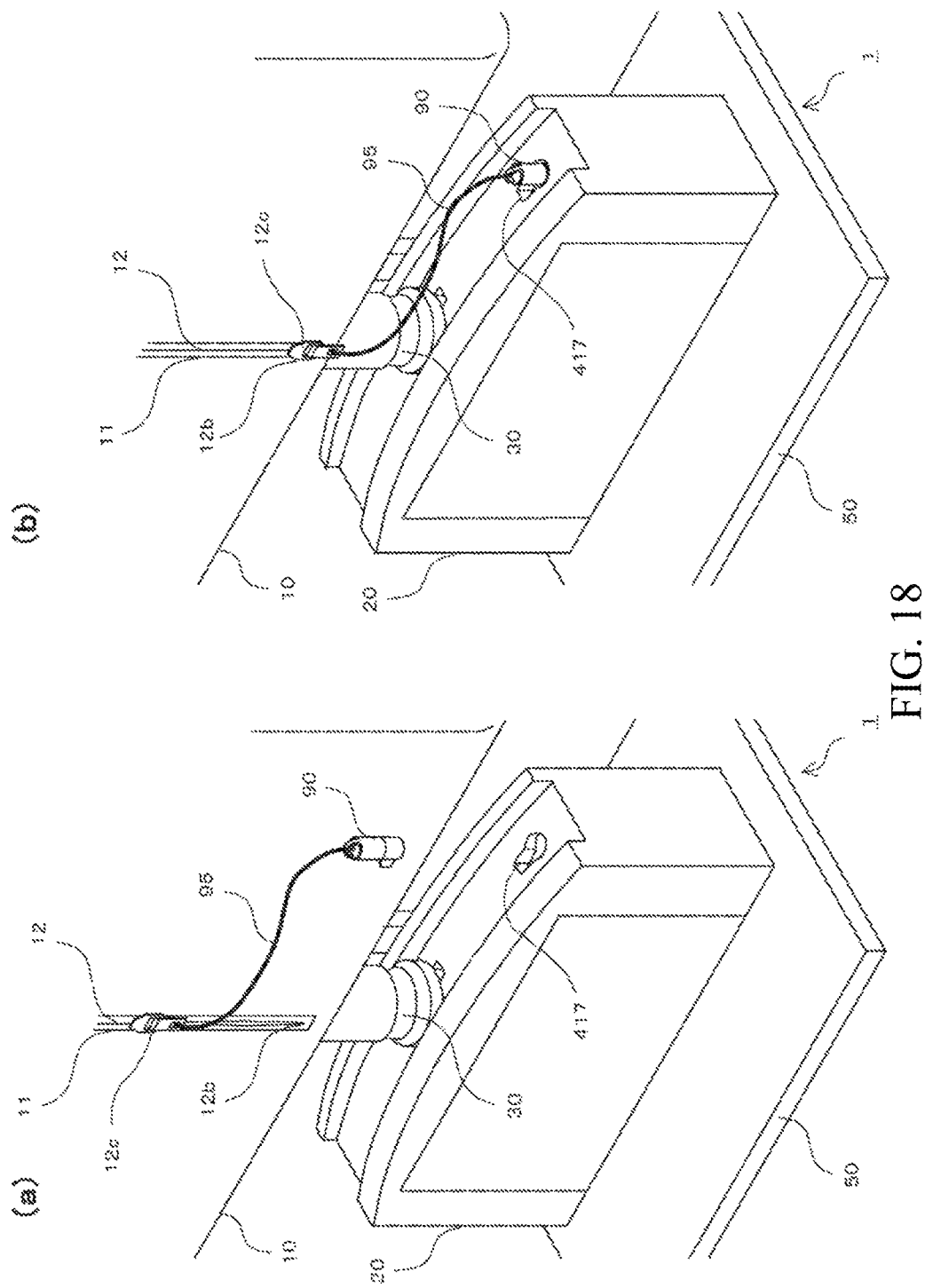
FIG. 18 is a diagram illustrating an action that a lock detection part detects that a throwing inlet of a bag body is locked by a zipper of the embodiments.
Figure 19:
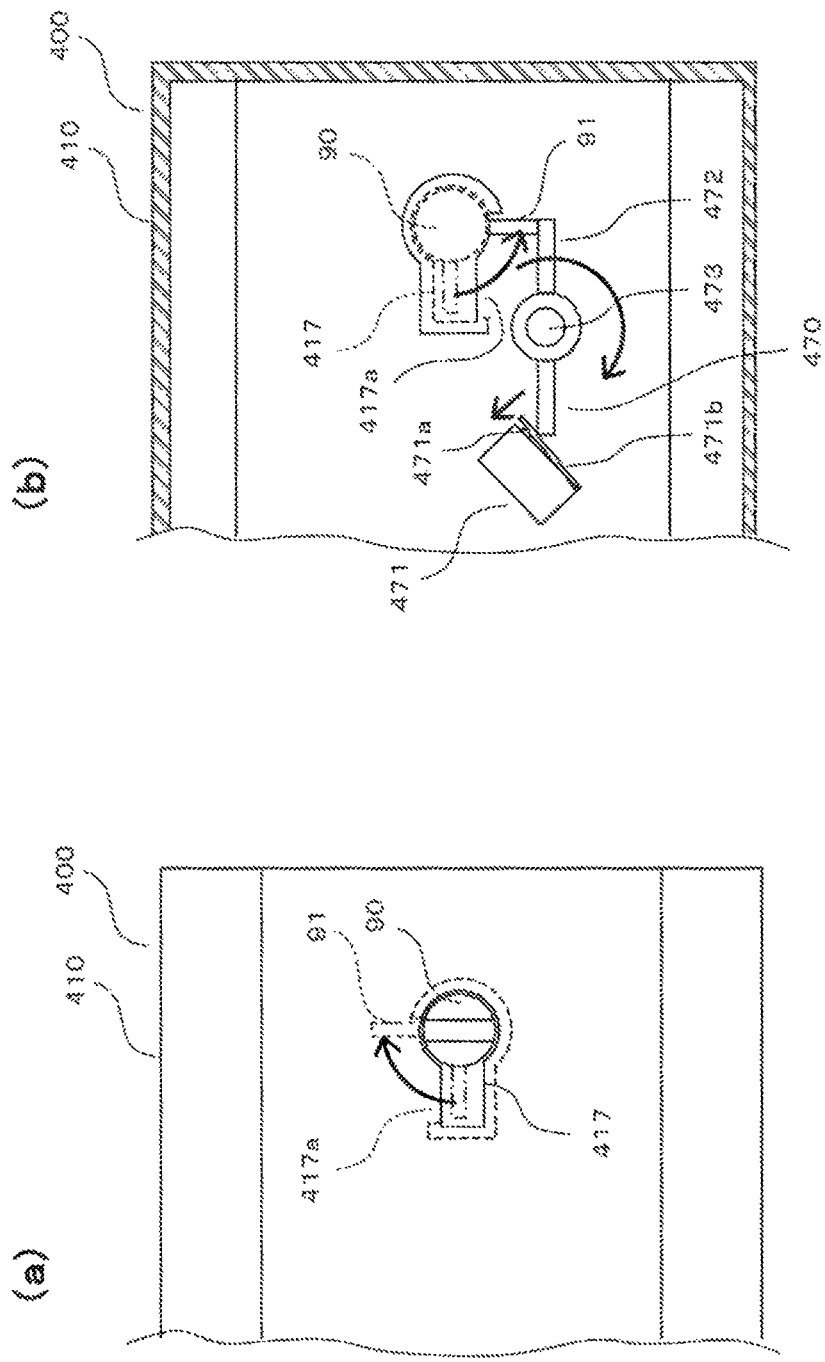
FIG. 19 is a diagram illustrating an action that a lock detection part detects that a throwing inlet of a bag body is locked by a zipper of the embodiments.

Next, referring to FIGS. 18 to 19, an action that a lock detection part 470 detects that a throwing inlet 11 of a bag body 10 is locked by a zipper 12 is described. It should be noted that the detection lock 90, the connecting rope 95, the lock inserting concave part 417 and the lock detection part 470 form the locking detection unit of the present disclosure.

A connecting rope 95 for connecting the detection lock 90 and the slider 12c has a length that enables the detection lock 90 to arrive at the lock inserting concave part 417 when the zipper 12 is locked near the end 12b. Therefore, as shown in FIG. 18(a), when the slider 12c is not located near the end 12b, the detection lock 90 fails to reach the lock inserting concave part 417 and the detection lock 90 cannot be inserted into the lock inserting concave part 417. Namely, at least in a state that the zipper 12 is completely pulled, the detection lock 90 fails to reach to the lock inserting concave part 417. On the other hand, as shown in FIG. 18(b), in a state that the zipper 12 is completely closed, the detection lock 90 can reach to the lock inserting concave part 417 and the detection lock 90 is inserted into the lock inserting concave part 417.

When the user locks the entire throwing inlet 11 through the zipper 12, as shown in FIG. 19(a), the detection lock 90 is inserted into the lock inserting concave part 417 and the inserted detection lock 90 rotates to the right in a top view. As shown in FIG. 19(b), the protruding part 91 of the detection lock 90 moves to the inner of the upper surface of the shell body 410 through the opening 417a, and one end of the relay rod 472 is pressed through the moved protrusion part 91. The relay rod 472 rotates; the rod 471b is pressed through the other end of the relay rod 472; and the switch 471a is pressed by the pressed rod 471b. Thus, the detection switch 471 detects that the detection lock 90 is inserted into the lock inserting concave part 417, i.e., detects that the throwing inlet 11 of the bag body 10 is locked by the zipper 12.

It should be noted that when the detection lock 90 is removed from the lock inserting concave part 417, the rod 471b rotates the relay rod 472 through its elasticity, and simultaneously returns to an initial position. Thus, the detection switch 471 detects that the detection lock 90 is removed from the lock inserting concave part 417.

A detailed structure of the fragrance supply unit 80 is described below.

Figure 20:
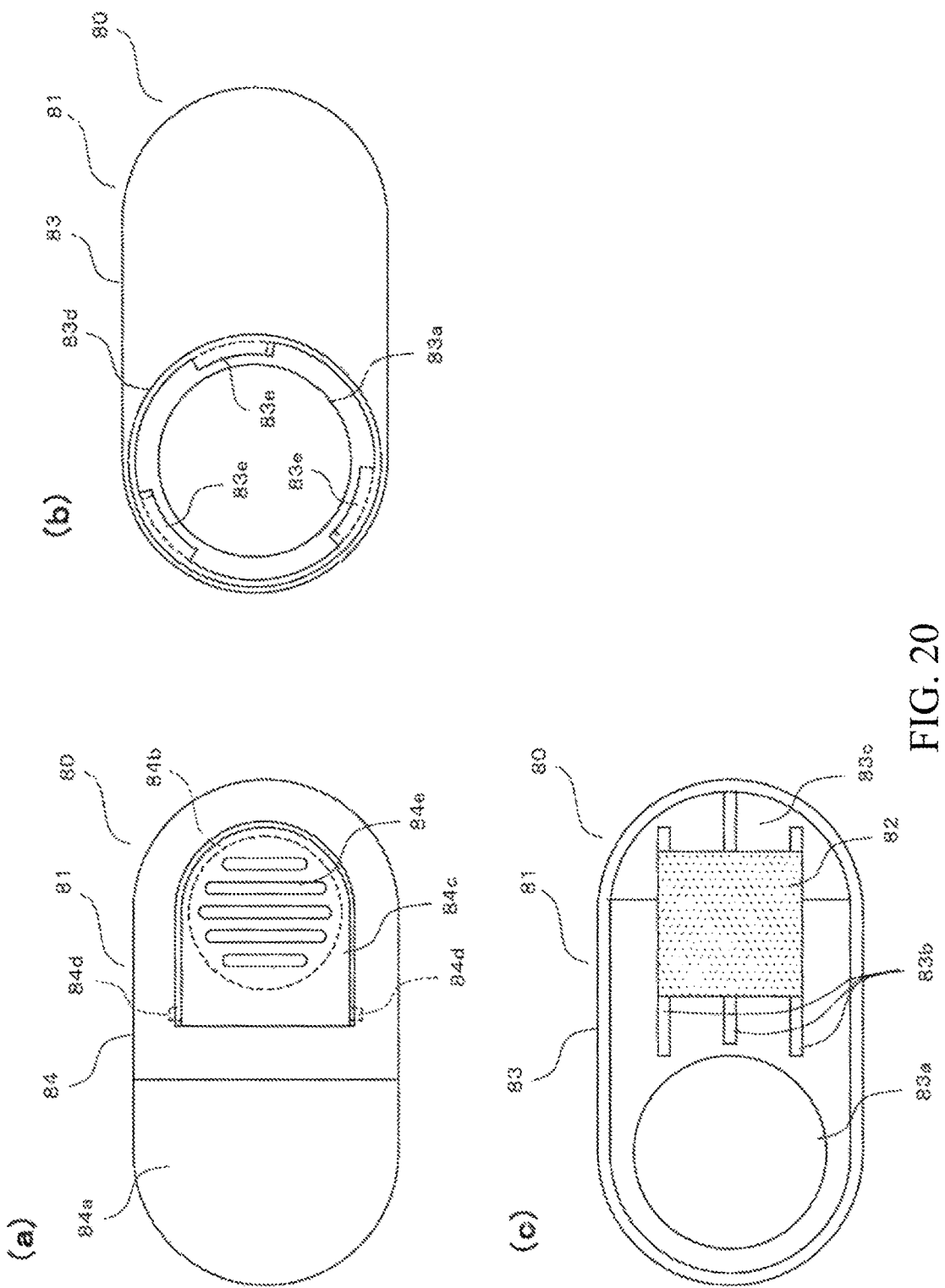
FIG. 20 is a structural diagram illustrating a fragrance supply unit of the embodiments.
Figure 21:
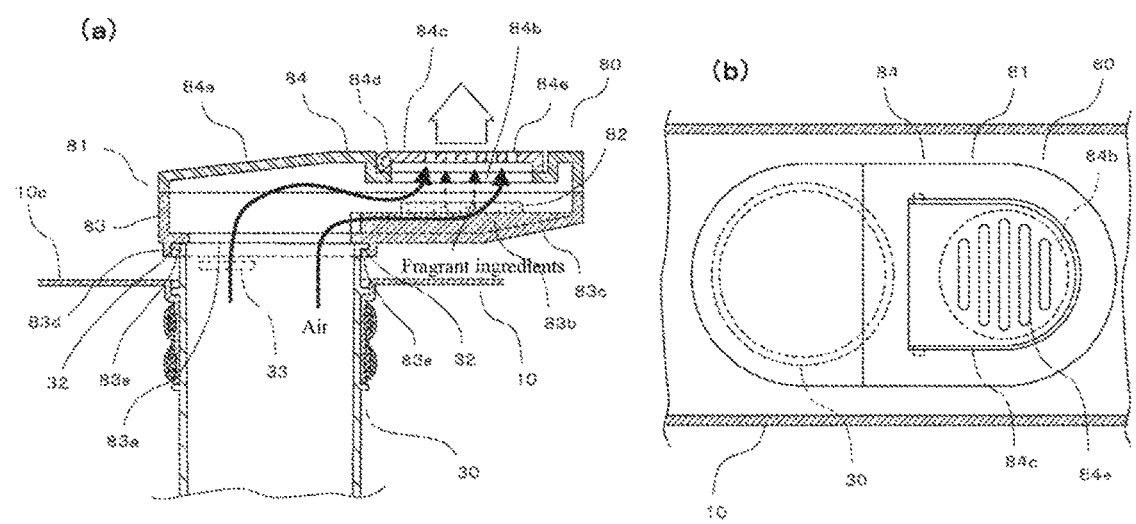
FIG. 21 is a structural diagram illustrating a fragrance supply unit of the embodiments.

FIGS. 20 and 21 are structural diagrams illustrating a fragrance supply unit 80. FIGS. 20(a) and (b) are a top view and a bottom view illustrating a fragrance supply unit 80 respectively. FIG. 20(c) is a top view illustrating a fragrance supply unit 80 in a state that an upper box body 84 is removed. FIG. 21 is a longitudinal section view illustrating a central and lower part of a bag body 10 in a state that a fragrance supply unit 80 is installed on an induction pipe 30. FIG. 21(b) is a transverse section view illustrating a central and lower part of a bag body 10 in a state that a fragrance supply unit 80 is installed on an induction pipe 30.

The fragrance supply unit 80 includes an accommodating box 81 which has an oval box shape in a top view, and a fragrant body 82 accommodated in the accommodating box 81. The accommodating box 81 includes a lower box body 83 with an opened upper surface and an upper box body 84 with an opened bottom surface.

At the bottom surface of the lower box body 83, an air suction port 83a is formed at one end along a long edge direction, and ribs 83b adjacent to the air suction port 83a and extending to the long edge direction are formed. The fragrant body 82 is loaded above the ribs 83b. In addition, on the other end, the bottom surface of the lower box body 83 has an inclined surface 83c which becomes higher to the other end. Moreover, at the bottom surface of the lower box body 83, a cylindrical connecting port 83d is formed in a manner of encircling the air suction port 83a. Claw parts 83e are formed in positions of the connecting port 83d corresponding to the clamping pieces 32 of the induction pipe 30.

The upper box body 84 is installed on the upper surface of the lower box body 83. The upper surface of the upper box body 84 has an inclined surface 84a which becomes higher to the other end in a position opposite to the air suction port 83a. In addition, an opening 84b is formed in a position opposite to ribs 83b on the upper surface of the upper box body 84. The opening 84b is covered by a cover 84c in an openable and closable manner. The cover 84c rotates by taking a hinge 84d as a center. Slit-shaped vent holes 84e are formed in the cover 84c.

The fragrant body 82 is formed by porous material and the like which can be immersed in a liquid flavoring agent. The cover 84c is opened and the fragrant body 82 is placed in the accommodating box 81 through the opening 84b.

When the fragrance supply unit 80 is installed on the induction pipe 30, the connecting port 83d is inserted into the top of the induction pipe 30 in a state that the claw parts 83e and the clamping pieces 32 are staggered. Then, the fragrance supply unit 80 rotates to a position where the claw parts 83e and the clamping pieces 32 overlap. As shown in FIG. 21(a), the clamping pieces 32 and the claw parts 83e are clamped, and the fragrance supply unit 80 does not fall upwards. It should be noted that the existence of the front flange part 33 and the rear flange part 34 can prevent the side fabric 10c of the lower surface of the bag body 10 from being engaged between the connecting port 83d and the induction pipe 30.

As shown in FIG. 21(b), in a state that the fragrance supply unit 80 is installed on the induction pipe 30, the fragrance supply unit 80 is configured in the bag body 10 in such a manner that a long edge direction of the fragrance supply unit 80 forms a left-right direction of the bag body 10. As mentioned above, since the induction pipe 30 is fixed to the cylindrical part 15 in a manner of not rotating relative to the bag body 10, the fragrance supply unit 80 correctly installed on the induction pipe 30 does not come into contact with the front surface and the rear surface of the bag body 10.

The deodorization operation and fragrance increasing operation performed by the clothes deodorizing apparatus 1 are described below.

In the deodorization operation, the clothes hung on the clothes rack H for clothes are accommodated into the bag body 10 hung on the bag body holding part 70. At this moment, as shown in FIG. 10(b), the clothes in the bag body 10 are hung to the second holding part 121 of the clothes rack holding part 42 with the clothes rack H. In this way, in the bag body 10, the clothes are hung through the clothes rack holding part 42. The deodorization button 452 of the operation part 450 is pressed. When the pipe detection switch 460 detects that the induction pipe 30 is installed on the ozone supply apparatus 20, and the lock detection part 470 detects that the lock 90 is inserted into the lock inserting concave part 417, i.e., when a condition that the throwing inlet 11 of the bag body 10 is locked by the zipper 12 is detected, the control unit 900 starts the deodorization operation to enable the blowing fan 700 and the ozone generator 600 to operate. When the induction pipe 30 is not installed on the ozone supply apparatus 20, the control unit 900 does not start the deodorization operation and enables the first informing part 454 to illuminate. In addition, when the throwing inlet 11 is not locked, the control unit 900 does not start the deodorization operation and enables the second informing part 455 to illuminate a lamp.

When the deodorization operation starts, outside air is taken into the air suction pipe 810 through the air suction port 418, the dust and ozone included in the air are removed through the dust filter 820 and the ozone removing filter 830 in the air suction pipe 810. The air without dust and ozone is delivered into the vent pipe 500 through the blowing fan 700 (with reference to an arrow in FIG. 16(b)). The air flowing in the vent pipe 500 is mixed with the ozone generated by the ozone generator 600 when passing through the ozone generator 600. In this way, ozone-containing air arrives at the exhaust port 414 through the vent pipe 500 and is exhausted through the exhaust port 414 (with reference to an arrow in FIG. 16(a)).

The ozone-containing air exhausted from the ozone supply apparatus 20 is guided into the bag body 10 through the induction pipe 30. As shown by an arrow in FIG. 1(a), the ozone-containing air guided into the bag body 10 flows and contacts with the clothes in the bag body 10 from bottom to top. The clothes are deodorized through a deodorization function of the ozone included in the air. Herein, although the lower part of the clothes is opened greatly, the ozone-containing air flowing from bottom to top in the bag body 10 can easily spread over the inner of the clothes. Thus, a thorough deodorization can be performed on the outer and inner sides of the clothes.

In addition, since the bag body 10 is hung to the bag body holding part 70 and the clothes are hung on the clothes rack H for clothes, a clearance between the upper part of the bag body 10 and a shoulder part of the clothes is ensured. Thus, since the ozone can easily spread over the shoulder part of the clothes, the deodorization effect can be enhanced.

The air, in which the concentration of ozone is reduced due to the deodorization for the clothes, as shown by a dotted arrow in FIG. 1(a), is exhausted from the bag body 10 through the exhaust part 41 in the upper part of the bag body 10. Ozone is removed from the air after deodorization through the ozone removing filter 44 when the air after deodorization passes through the exhaust part 41. Thus, the concentration of the ozone in the air exhausted from the bag body 10 is further reduced.

Next, under a condition of performing fragrance increasing operation, the user accommodates the clothes into the bag body 10 hung on the bag body holding part 70. Moreover, as shown in FIG. 21, in the bag body 10, the fragrance supply unit 80 provided with the fragrant body 82 is installed on the induction pipe 30. The fragrance increasing button 453 of the operation part 450 is pressed. When the pipe detection switch 460 detects that the induction pipe 30 is installed on the ozone supply apparatus 20, and when the lock detection part 470 detects that the throwing inlet 11 of the bag body 10 is locked by the zipper 12, the control unit 900 starts the fragrance increasing operation and enables the blowing fan 700 to operate. When the induction pipe 30 is not installed on the ozone supply apparatus 20, the control unit 900 does not start the fragrance increasing operation and enables the first informing part 454 to illuminate a lamp. In addition, when the throwing inlet 11 is not locked, the control unit 900 does not start the fragrance increasing operation and enables the second informing part 455 to illuminate a lamp.

When the fragrance increasing operation starts, as shown in FIG. 21(a), the air exhausted from the induction pipe 30 is introduced into the accommodating box 81 from the air suction port 83a. The introduced air flows upwards after flowing towards the other end along the ribs 83b. Through the air that passes through the fragrant body 82, fragrant ingredients included in the fragrant body 82 volatilize and are mixed into the air. The air with the fragrant ingredients is exhausted into the bag body 10 through the opening 84b and the vent hole 84e. It should be noted that the air successfully flows in the accommodating box 81 through two inclined surfaces 83c and 84a, arranged on the accommodating box 81.

Like the deodorization operation, the air with the fragrant ingredients flows from bottom to top in the bag body 10. In addition, since the air pressure in the bag body 10 is increased, a fragrance increasing effect of the clothes can be enhanced.

Effects of Present Embodiment

The following effects can be achieved through the present embodiment.

(1) Since the clothes deodorizing apparatus 1 adopts such a structure that the ozone-containing air is supplied from the ozone supply apparatus 20 and the air with the fragrant ingredients is supplied to the bag body 10 for accommodating the clothes to perform deodorization and fragrance increasing operations on the clothes, clothes deodorizing apparatus 1 can be easily arranged in a house without a large arrangement space.

(2) The locking detection unit, which includes the detection lock 90, the connecting rope 95, the lock inserting concave part 417 and the lock detection part 470 enables to detect that the throwing inlet 11 of the bag body 10 is locked by the zipper 12.

(3) Since the deodorization operation and the fragrance increasing operation are not performed in case of not detecting that the throwing inlet 11 is locked by the zipper 12, the deodorization operation and the fragrance increasing operation in a state that the throwing inlet 11 is opened can be prevented.

(4) Since the following structure is adopted, the locking detection unit capable of detecting the locking of the throwing inlet 11 on an ozone supply apparatus 20 separated from the bag body 10 can be realized: the detection lock 90 is connected with the slider 12c of the zipper 12 through the connecting rope 95 in a manner of not reaching the lock inserting concave part 417 in a state that the zipper 12 is completely opened and reaching the lock inserting concave part 417 in a state that the zipper 12 is completely closed; and the lock detection part 470 detects that the detection lock 90 is inserted into the lock inserting concave part 417. Thus, a locking of the throwing inlet 11 by the zipper 12 is detected.

(5) Since the lock detection part 470 is designed to include the detection switch 471 and the relay rod 472, and the detection switch 471 detects insertion of the lock inserting concave part 417 into the detection lock 90 via the relay rod 472, the detection switch 471 can be prevented from directly contacting with the user through the lock inserting concave part 417, and the detection switch 471 can be prevented from being damaged due to static electricity and the like.

(6) Since a pull-down direction of the slider 12c is set as the locking direction of the throwing inlet 11, in a locking state of the throwing inlet 11, self weight of the slider 12c acts in the locking direction. Therefore, a hidden danger that a closed part of the zipper 12 is opened due to the self weight of the slider 12c does not exist, and the ozone-containing air can hardly leak from the closed part.

Alternative Embodiments

Although embodiments and their alternatives regarding the present disclosure are described above, the present disclosure is not limited to the above-mentioned embodiments. In addition to the above, various alternatives can also be made to embodiments of the present disclosure.

Figure 22:
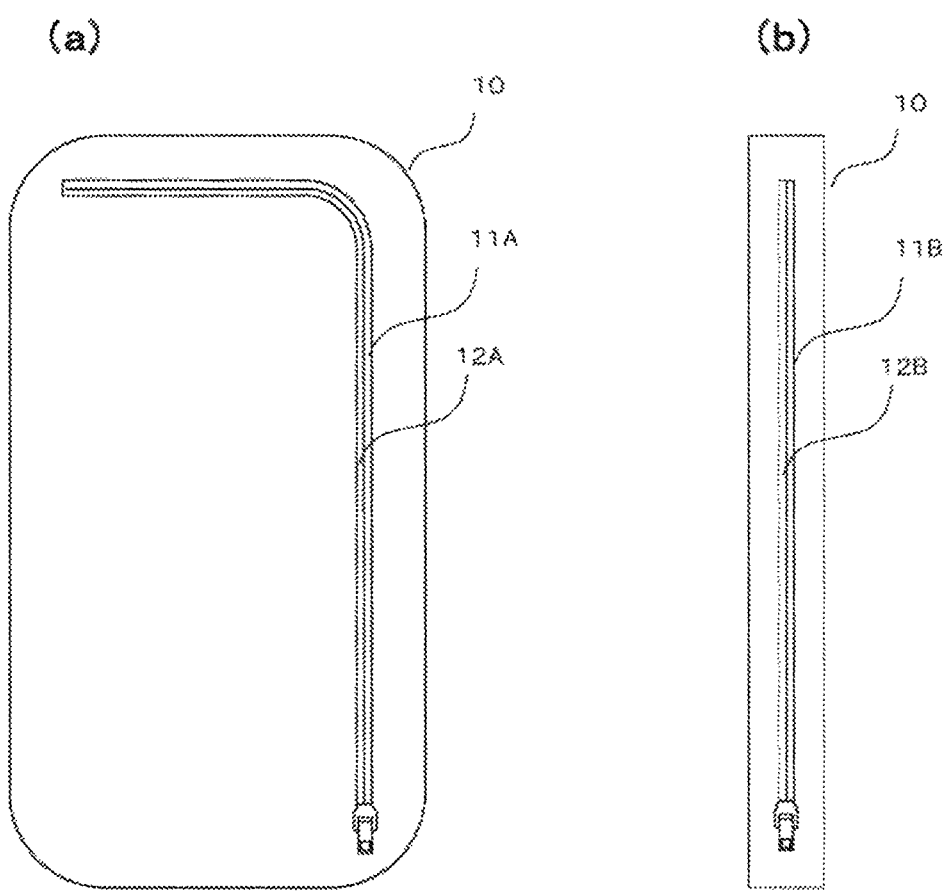
FIG. 22 is a structural diagram illustrating a clothes deodorizing apparatus of the alternative embodiments.

For example, in above embodiments, in the center of the front surface of the bag body 10, a gap which straightly extends in an up-down direction as the throwing inlet 11 is formed. The throwing inlet 11 is opened and closed by the zipper 12, but is not limited to this. For example, as shown in FIG. 22(a), on the front surface of the bag body 10, a gap which extends along the upper surface and the side surface of the bag body 10 is formed as the throwing inlet 11A; and the throwing inlet 11A is opened and closed by the zipper 12A having a shape corresponding to the throwing inlet 11A. Or the throwing inlet 11B which straightly extends in the up-down direction like the above embodiment, and the zipper 12B can also be arranged on the left side surface or the right side surface of the bag body 10.

In addition, in above embodiments, the closed direction of the zipper 12 is set as a top-to-bottom direction of the bag body 10. However, the closed direction of the zipper 12 can also be set as a bottom-to-top direction of the bag body 10. In examples shown in FIGS. 22(a) and (b), the opened direction and the closed direction may be any direction.

Then, in above embodiments, the locking detection unit adopts the following structure: the detection lock 90 has the protruding part 91 that protrudes from a circumferential surface of a cylindrical body; the detection lock 90 is inserted into the lock inserting concave part 417 and then rotates, so that the relay rod 472 rotates through the protruding part 91; and the detection switch 471 is pressed through the relay rod 472. However, the structure of the locking detection unit can also adopt, for example, the structures shown in FIGS. 23(a) and (b).

Figure 23:
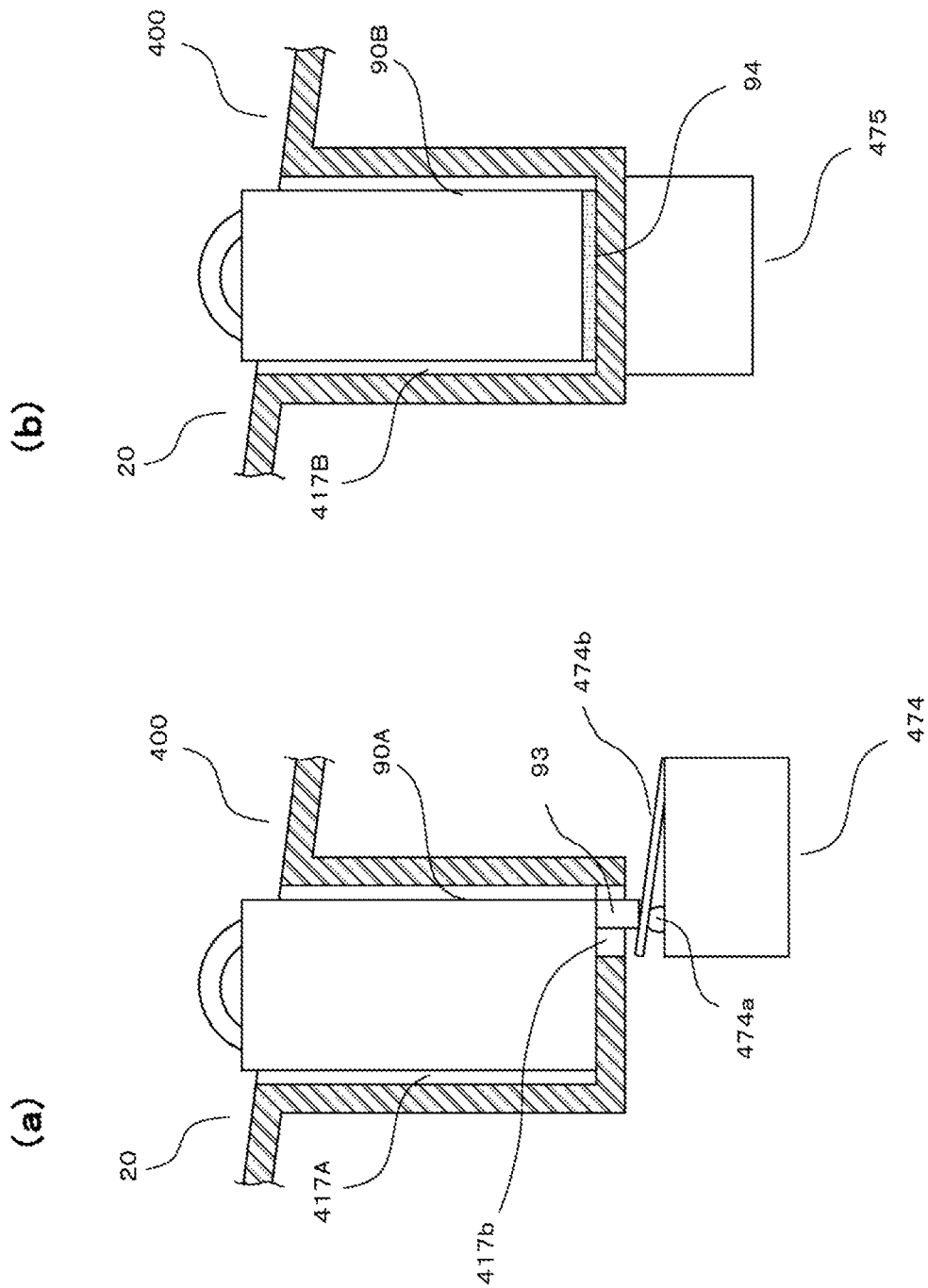
FIG. 23 is a structural diagram illustrating a clothes deodorizing apparatus of the alternative embodiments.

The bottom surface of the cylindrical body of the structure in FIG. 23(a) has a detected body 90A with the protruding part 93. An inserting concave part 417A having a shape corresponding to the detected body 91A is formed on the upper surface of the shell 400 of the ozone supply apparatus 20; and an inserting hole 417b for the protruding part 93 to pass through is formed in the bottom surface of the inserting concave part 417A. The detection switch 474 including a switch part 474a and a rod part 474b is arranged under the inserting concave part 417A. Like above embodiments, the detected body 90A is connected with the slider 12c of the zipper 12 through the connecting rope 95. After the throwing inlet 11 is locked by the zipper 12, when the detected body 90A is inserted into the inserting concave part 417A, the switch part 474a is pressed by the protruding part 93 by means of the rod part 474b. Thus, the detection switch 474 detects the locking of the throwing inlet 11.

The bottom surface of the cylindrical body of the structure in FIG. 23(b) has a detected body 90B equipped with a magnet 94. An inserting concave part 417B having a shape corresponding to the detected body 91B is formed on the upper surface of the shell 400 of the ozone supply apparatus 20; a detection switch which acts through magnetic force is arranged under the inserting concave part 417B, such as a reed switch 475. Like above embodiments, the detected body 90B is connected with the slider 12c of the zipper 12 through the connecting rope 95. After the throwing inlet 11 is locked by the zipper 12, when the detected body 90B is inserted into the inserting concave part 417B, the magnet 94 is close to the reed switch 475. Thus, the reed switch 475 detects the locking of the throwing inlet 11.

In addition, various appropriate modifications can be made to embodiments of the present disclosure within a scope of concept of the appended claims.

LIST OF REFERENCE NUMERALS

10: bag body; 11: throwing inlet; 12: zipper; 12c: slider; 20: ozone supply apparatus; 90: detection lock (detected body); 414: exhaust port; 417: lock inserting concave part (accepting part); 470: lock detection part (detection part); 471: detection switch; 472: relay rod; 500: vent pipe; 600: ozone generator; 700: blowing fan; and 900: control unit (control part).

What is claimed is:

1. A clothing treatment apparatus, comprising:
    a bag body configured to accommodate clothes;
    an ozone supply apparatus configured to supply ozone-containing air into the bag body;
    a throwing inlet arranged on the bag body and configured to be opened and closed through a zipper; and
    a locking detection unit configured to detect that the throwing inlet is closed by the zipper;
    wherein the locking detection unit comprises: a detected body connected with a slider of the zipper; an accepting part arranged on the ozone supply apparatus and configured to accept the detected body; and a detection part arranged on the ozone supply apparatus and configured to detect the detected body accepted by the accepting part;
    wherein the detected body is configured to not insert into the accepting part in a state where the zipper is opened and configured to insert into the accepting part in a state where the zipper is closed; and
    the detection part comprises a relay rod and a detection switch, the relay rod is configured to be pressed and moved by the detected body in a state where the detected body is accepted by the accepting part; the detection switch is configured to be pressed by the relay rod through movement of the relay rod.

2. The clothing treatment apparatus according to claim 1, wherein
    the zipper is arranged on the throwing inlet in such a manner that the throwing inlet is closed when the slider of the zipper is pulled downwards and the throwing inlet is opened when the slider is pulled upwards.

3. The clothing treatment apparatus according to claim 1, wherein
    the ozone supply apparatus comprises:
    an exhaust port configured to exhaust the ozone-containing air supplied into the bag body;
    an ozone generator;

a blowing fan configured to deliver air to the ozone generator;

a vent pipe configured to guide the ozone-containing air generated by the ozone generator to the exhaust port; and a control part configured to control the ozone generator and the blowing fan, wherein the control part is configured to enable the ozone generator and the blowing fan to operate based on a closed state of the throwing inlet detected by the locking detection unit.

4. The clothing treatment apparatus according to claim 2, wherein the ozone supply apparatus comprises:

an exhaust port configured to exhaust the ozone-containing air supplied into the bag body;

an ozone generator;

a blowing fan configured to deliver air to the ozone generator;

a vent pipe configured to guide the ozone-containing air generated by the ozone generator to the exhaust port; and a control part configured to control the ozone generator and the blowing fan, wherein the control part is configured to enable the ozone generator and the blowing fan to operate based on a closed state of the throwing inlet detected by the locking detection unit.

* * * * *

UNITED STATES PATENT AND TRADEMARK OFFICE
CERTIFICATE OF CORRECTION

| | |
|---|---|
| PATENT NO. | : 10,086,103 B2 |
| APPLICATION NO. | : 15/573384 |
| DATED | : October 2, 2018 |
| INVENTOR(S) | : Shigeharu Nakamoto et al. |

It is certified that error appears in the above-identified patent and that said Letters Patent is hereby corrected as shown below:

On the Title Page

In Item (73), under "Assignee", beneath "Aqua Co., Ltd", insert -- Qingdao Haier Washing Machine Co., Ltd. --.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*